US008715926B2

(12) United States Patent
Duerksen-Hughes et al.

(10) Patent No.: US 8,715,926 B2
(45) Date of Patent: May 6, 2014

(54) BIOMARKERS FOR THE DETECTION OF HEAD AND NECK TUMORS

(75) Inventors: Penelope J. Duerksen-Hughes, Redlands, CA (US); Maria Filippova, Riverside, CA (US); Valeri Filippov, Riverside, CA (US)

(73) Assignee: Loma Linda University, Loma Linda, CA (US)

( * ) Notice: Subject to any disclaimer, the term of this patent is extended or adjusted under 35 U.S.C. 154(b) by 27 days.

(21) Appl. No.: 13/130,934

(22) PCT Filed: Nov. 24, 2009

(86) PCT No.: PCT/US2009/065796
§ 371 (c)(1),
(2), (4) Date: May 24, 2011

(87) PCT Pub. No.: WO2010/060103
PCT Pub. Date: May 27, 2010

(65) Prior Publication Data
US 2011/0229876 A1 Sep. 22, 2011

Related U.S. Application Data

(60) Provisional application No. 61/117,492, filed on Nov. 24, 2008.

(51) Int. Cl.
*C12Q 1/68* (2006.01)
(52) U.S. Cl.
USPC ........................................................ 435/6.1
(58) Field of Classification Search
None
See application file for complete search history.

(56) References Cited

PUBLICATIONS

Li et al., Journal of Clinical Oncology, 2006, vol. 24, pp. 1754-1760.*
Smeets et al., International Journal of Cancer, 2007, vol. 121, pp. 2465-2472.*
Pyeon et al., Cancer Research, 2007, vol. 67, pp. 4605-4619.*
Pyeon et al., Cancer Research, 2007, vol. 67, supplemental data pp. 1-61.*
Capone R B et al: "Detection and quantitation of human papillomavirus (HPV) DNA in the sera of patients with HPV-associated head and neck squamous cell carcinoma," Clinical Cancer Research, The American Association for Cancer Research, US, vol. 6, No. 11, Nov. 1, 2000, pp. 4171-4175, XP002488445.
Dong S M et al: "Epigenetic inactivation of RASSF1A in head and neck cancer," Clinical Cancer Research 20031001 US, vol. 9, No. 10 I, Oct. 1, 2003, pp. 3635-3640, XP9157685.

Martinez et al: "Identification of differentially expressed genes in HPV-positive and HPV-negative oropharyngeal squamous cell carcinomas," European Journal of Cancer, Pergamon Press, Oxford, GB, vol. 43, No. 2, Jan. 23, 2007, pp. 415-432, XP005856092.
Pyeon D et al: "Fundamental differences in cell cycle deregulation in human papillomavirus-positive and human papillomavirus-negative head/neck and cervical cancers", Cancer Research, American Association for Cancer Research, US, vol. 67, No. 10, May 15, 2007, pp. 4605-4619, XP002508007.
Schlecht NF et al: "Gene expression profiles in HPV-infected head and neck cancer", The Journal of Pathology, vol. 213, No. 3, Nov. 1, 2007, pp. 283-293, XP55022397.
Seligmann Bruce: "A multiplexed, quantitative, extraction-free, gene expression assay," American Biotechnology Laboratory, vol. 23, No. 7, Jun. 2005, pp. 20-21, XP009157586.
Slebos R J C et al: "Gene expression differences associated with human papillomavirus status in head and neck squamous cell carcinoma," Clinical Cancer Research, The American Association for Cancer Research, US, vol. 12, No. 3 Pt 1, Feb. 1, 2006, pp. 701-709, XP002508008.
Zhao Ming et al: "Feasibility of quantitative PCR-based saliva rinse screening of HPV for head and neck cancer,". International Journal of Cancer, vol. 117, No. 4, Nov. 20, 2005, pp. 605-610, XP55022369.
Loma Linda University et al., European Search Report issued in corresponding European Patent Application No. 0982839.2 on Apr. 2, 2012.
Loma Linda University et al., International Search Report and Written Opinion issued on Mar. 24, 2010 for International Patent Application No. PCT/US09/65796.
Li et al., "Serum circulating human mRNA profiling and its utility for oral cancer detection," Journal of Clinical Oncology 2006, 24(11):1754-1760; p. 1756, par. 8-9; p. 1757, par. 1-2.
Marais et al., "Oral antibodies to human papillomavirus type 16 in women with cervical neoplasia," Journal of Medical Virology 2001, 65:149-154; p. 150, par. 2.
Righini et al., "Tumor-specific methylation in saliva: a promising biomarker for early detection of head and neck cancer recurrence," Clin. Cancer Res. 2007, 13(4): 1179-1185; p. 1180, par. 5; p. 1181, par. 3; p. 1182, par. 4.
Smeets et al., "A novel algorithm for reliable detection of human papillomavirus in parafin embedded head an neck cancer specimen," Int. J. Cancer 2007, 121:2465-2472; Table I, Table II, p. 2466, par. 2-3, 5, 7; p. 2467, par. 2; p. 2468, par. 2-5.
Wiest et al., "Involvement of intact HPV16 E6/E7 gene expression in head and neck cancers with unaltered p53 status and perturbed pRb cell cycle control," Oncogene 2002, 21:1510-1517; Abstract, Table 3, p. 1516, par. 2, 7.
Wong et al., "Toward a simple, saliva-based test for the detection of oral cancer," Expert Rev. Mol. Diagn. 2006, 6 (3):267-272; p. 268, par. 3; p. 269, par. 2-7.

\* cited by examiner

*Primary Examiner* — Anne Gussow
*Assistant Examiner* — Mindy G Brown
(74) *Attorney, Agent, or Firm* — David A. Farah; Sheldon Mak & Anderson PC

(57) ABSTRACT

A method of detecting the presence of specific human papilloma virus and host cell biomarkers associated with head and neck tumors in biological samples, like saliva, blood or biopsy tissue, obtained from a subject.

7 Claims, 5 Drawing Sheets

_US 8,715,926 B2_

```
                         SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: GADH sense primer

<400> SEQUENCE: 1
tgcaccacca actgcttagc                                                   20

<210> SEQ ID NO 2
<211> LENGTH: 21
<212> TYPE: DNA
<213> ORGANISM: Artificial Sequence
<220> FEATURE:
<223> OTHER INFORMATION: GADPH antisense primer

<400> SEQUENCE: 2
ggcatggact gtggtcatga g                                                 21

<210> SEQ ID NO 3
<211> LENGTH: 22
<212> TYPE: DNA
<213> ORGANISM: Artificial Sequence
<220> FEATURE:
<223> OTHER INFORMATION: CDKN2A sense primer

<400> SEQUENCE: 3
agaaacctcg ggaaacttag at                                                22
```

```
<210> SEQ ID NO 4
<211> LENGTH: 22
<212> TYPE: DNA
<213> ORGANISM: Artificial Sequence
<220> FEATURE:
<223> OTHER INFORMATION: CDKN2A antisense primer

<400> SEQUENCE: 4
ctacgttaaa aggcaggaca tt                                              22

<210> SEQ ID NO 5
<211> LENGTH: 22
<212> TYPE: DNA
<213> ORGANISM: Artificial Sequence
<220> FEATURE:
<223> OTHER INFORMATION: DAPK1 sense primer

<400> SEQUENCE: 5
gcaaagtaca acaccagtaa cg                                              22

<210> SEQ ID NO 6
<211> LENGTH: 22
<212> TYPE: DNA
<213> ORGANISM: Artificial Sequence
<220> FEATURE:
<223> OTHER INFORMATION: DAPK1 antisense primer

<400> SEQUENCE: 6
caggttgatt ttgaacacag ag                                              22

<210> SEQ ID NO 7
<211> LENGTH: 22
<212> TYPE: DNA
<213> ORGANISM: Artificial Sequence
<220> FEATURE:
<223> OTHER INFORMATION: GSTP1 sense primer

<400> SEQUENCE: 7
tccctcatct acaccaacta tg                                              22

<210> SEQ ID NO 8
<211> LENGTH: 21
<212> TYPE: DNA
<213> ORGANISM: Artificial Sequence
<220> FEATURE:
<223> OTHER INFORMATION: GSTP1 antisense primer

<400> SEQUENCE: 8
agtccagcag gttgtagtca g                                               21

<210> SEQ ID NO 9
<211> LENGTH: 20
<212> TYPE: DNA
<213> ORGANISM: Artificial Sequence
<220> FEATURE:
<223> OTHER INFORMATION: KLK10 sense primer

<400> SEQUENCE: 9
atgagcacga tctcatgttg                                                 20

<210> SEQ ID NO 10
<211> LENGTH: 22
<212> TYPE: DNA
<213> ORGANISM: Artificial Sequence
<220> FEATURE:
<223> OTHER INFORMATION: KLK10 antisense primer
```

```
<400> SEQUENCE: 10
gaagacctca cactctttag gg                                              22

<210> SEQ ID NO 11
<211> LENGTH: 22
<212> TYPE: DNA
<213> ORGANISM: Artificial Sequence
<220> FEATURE:
<223> OTHER INFORMATION: SESN3 sense primer

<400> SEQUENCE: 11
actatacctg ggaaaatcat gg                                              22

<210> SEQ ID NO 12
<211> LENGTH: 22
<212> TYPE: DNA
<213> ORGANISM: Artificial Sequence
<220> FEATURE:
<223> OTHER INFORMATION: SESN3 antisense primer

<400> SEQUENCE: 12
agttctctca ggatagcagg tc                                              22

<210> SEQ ID NO 13
<211> LENGTH: 21
<212> TYPE: DNA
<213> ORGANISM: Artificial Sequence
<220> FEATURE:
<223> OTHER INFORMATION: Fas sense primer

<400> SEQUENCE: 13
gacatggctt agaagtggaa a                                               21

<210> SEQ ID NO 14
<211> LENGTH: 21
<212> TYPE: DNA
<213> ORGANISM: Artificial Sequence
<220> FEATURE:
<223> OTHER INFORMATION: Fas antisense primer

<400> SEQUENCE: 14
ttagtgtcat gactccagca a                                               21

<210> SEQ ID NO 15
<211> LENGTH: 21
<212> TYPE: DNA
<213> ORGANISM: Artificial Sequence
<220> FEATURE:
<223> OTHER INFORMATION: CFL1 sense primer

<400> SEQUENCE: 15
ccttcccaaa ctgcttttga t                                               21

<210> SEQ ID NO 16
<211> LENGTH: 21
<212> TYPE: DNA
<213> ORGANISM: Artificial Sequence
<220> FEATURE:
<223> OTHER INFORMATION: CFL1 antisense primer

<400> SEQUENCE: 16
ctggtcctgc ttccatgagt a                                               21
```

```
<210> SEQ ID NO 17
<211> LENGTH: 22
<212> TYPE: DNA
<213> ORGANISM: Artificial Sequence
<220> FEATURE:
<223> OTHER INFORMATION: NFKB1A sense primer

<400> SEQUENCE: 17
tgatcctgag ctccgagact tt                                              22

<210> SEQ ID NO 18
<211> LENGTH: 22
<212> TYPE: DNA
<213> ORGANISM: Artificial Sequence
<220> FEATURE:
<223> OTHER INFORMATION: NFKB1A antisense primer

<400> SEQUENCE: 18
agccctggta ggtaactctg tt                                              22

<210> SEQ ID NO 19
<211> LENGTH: 22
<212> TYPE: DNA
<213> ORGANISM: Artificial Sequence
<220> FEATURE:
<223> OTHER INFORMATION: CUTL1 sense primer

<400> SEQUENCE: 19
taactcttac agctttgcct tg                                              22

<210> SEQ ID NO 20
<211> LENGTH: 24
<212> TYPE: DNA
<213> ORGANISM: Artificial Sequence
<220> FEATURE:
<223> OTHER INFORMATION: CUTL1 antisense primer

<400> SEQUENCE: 20
ggaatccaaa ctagtgtgtt taga                                            24

<210> SEQ ID NO 21
<211> LENGTH: 24
<212> TYPE: DNA
<213> ORGANISM: Artificial Sequence
<220> FEATURE:
<223> OTHER INFORMATION: CDKN2B promoter region primer

<400> SEQUENCE: 21
tgtggttgag gaatcccgtc tcat                                            24

<210> SEQ ID NO 22
<211> LENGTH: 24
<212> TYPE: DNA
<213> ORGANISM: Artificial Sequence
<220> FEATURE:
<223> OTHER INFORMATION: CDKN2B promoter region primer

<400> SEQUENCE: 22
tgggaaagaa gggaagagtg tcgt                                            24

<210> SEQ ID NO 23
<211> LENGTH: 20
<212> TYPE: DNA
<213> ORGANISM: Artificial Sequence
<220> FEATURE:
<223> OTHER INFORMATION: SFRS6 forward primer
```

```
<400> SEQUENCE: 23
tgtgttttca aagacggtgg                                              20

<210> SEQ ID NO 24
<211> LENGTH: 20
<212> TYPE: DNA
<213> ORGANISM: Artificial Sequence
<220> FEATURE:
<223> OTHER INFORMATION: SFRS6 reverse primer

<400> SEQUENCE: 24
caggctttcg ctatatgggc                                              20
```

BIOMARKERS FOR THE DETECTION OF HEAD AND NECK TUMORS

STATEMENT REGARDING FEDERALLY SPONSORED RESEARCH OR DEVELOPMENT

This invention was made with United States Government support in part by the National Institute of Allergy and Infectious Diseases under Grant No. 1R43AI082815-01A1. The Government has certain rights in this invention.

CROSS-REFERENCE TO RELATED APPLICATIONS

The present application is a national stage of International Patent Application No. PCT/US2009/065796 filed on Nov. 24, 2009 and titled "Biomarkers for the Detection of Head and Neck Tumors, which claims the benefit of U.S. Provisional Patent Application No. 61/117,492 filed Nov. 24, 2008, now expired, the contents of which are incorporated herein by reference in their entirety.

BACKGROUND

Involvement of Human Papillomavirus (HPV) in Head and Neck Cancer (HNC)

Head and neck cancers arise in the mucosal epithelia that line the throat, oropharynx and mouth. Together, they represent the sixth most common cancer in the US; once diagnosed, patients have a survival rate of approximately 50% (1). It was estimated that 34,360 men and women (24,180 men and 10,180 women) would be diagnosed with and 7,550 men and women would die of cancer of the oral cavity and pharynx in 2007 (2). Approximately 20-30% of the HNC cases are linked to HPV; the remainder are thought to be linked to other risk factors such as tobacco and alcohol.

Human papillomavirus (HPV) is best known for its involvement in cervical cancer, and is believed to be responsible for more than 90% of these cancers (3). It has therefore been suggested that the presence of HPV could serve as a biomarker for cervical cancer (4). More recently, HPV has been implicated in the development of approximately 20%-30% of HNC as well (see (5) for a recent review), with some estimates in some areas as high as 75% (6-15). Furthermore, the proportion of oral squamous cell carcinomas that are HPV-related is thought to be increasing (16). Not all areas in the head and neck area are affected equally by HPV; the tonsillar area appears to be particularly susceptible, with one study showing 51% of tonsillar carcinomas to be HPV positive (17). Interestingly, while high-risk HPV sequences were detected in oral cells from 23% of patients in one study, these sequences were also detected in 11% of control subjects (14). This is consistent with findings in cervical cancer, where many more people are infected than actually develop cancer. For example, it is estimated that 10 million women in the US have cervical human papillomavirus infections, while only 15 thousand develop cancer.

The HPV Life Cycle

During the normal HPV life cycle, HPV enters the tissue through a cut or wound and thus comes in contact with the basal keratinocytes of the squamous epithelia. After entering the cells, it remains as a circular episome within this layer, expressing low levels of early viral proteins (including E6 and E7) and replicating its genome in concert with replication of the cellular genome. Typically, at this stage, viral RNA and DNA are found at very low levels, with 50-100 episomal copies per cell. As the cells move upward, they become increasingly differentiated into keratinocytes, and these changes in turn trigger changes in HPV activities. The virus enters the vegetative state, and begins to produce the L1 and L2 proteins that will provide the outer coat of the virus. Finally, at the top of the papilloma or wart, the dead cells that flake off will be filled with functional virions that have the ability to infect the next individual with whom they come in contact (see (18) for review). It is important to realize that integration into the human genome, and the cellular transformation that may follow (see below), is not a normal part of the viral life cycle. In fact, this set of events represents a dead end for the virus, as cancer tissue does not produce viable virions.

HPV Oncogenes and their Role in Oncogenesis

Not all types of HPV are associated with cancer development. Those that are not associated with cancer are considered to be "low-risk" (for example HPV 6 and HPV 11), while those known to be associated with cancer are "high-risk" (for example, HPV 16 and HPV 18). High-risk strains of human papillomaviruses code for two oncogenes; E6 and E7. Under normal, episomal conditions, E6 and E7 are expressed at low levels, and are thought to function by creating conditions in the infected keratinocytes that will favor replication of the virus and prevent apoptosis of the host cells. Their expression is negatively regulated, at least in part, by the E2 protein (19-23). However, under conditions that can lead to tumor formation, the activity of E2 is frequently lost, allowing increased expression of E6 and E7. At these higher levels, these two oncoproteins have major effects on a variety of cellular functions that can lead to uncontrolled growth of the expressing cell. E6 is best known for its ability to bind to and mediate the degradation of the tumor suppressor p53 (24). This is not the only activity of E6, however; E6 actually binds to many additional cellular proteins and can affect their biological activities (reviewed in (25, 26)). Several of these proteins, including p53, myc, bak, TNF R1, FADD and pro-caspase 8, are involved in cellular apoptotic pathways. As a consequence of these interactions, cells expressing E6 are much less likely to undergo apoptosis than are cells not expressing E6. E7 is best known for its ability to bind to and inactivate the tumor suppressor Rb protein (27, 28). However, like E6, E7 also has multiple cellular activities (29).

Most individuals who are infected with human papillomaviruses, even with high-risk papillomaviruses, never develop cancer. Rather, the infection proceeds as described above and is eventually cleared by the immune system. Work in the cervical cancer field has led to the development of a model for cancer development that involves the relatively rare (and possibly late) event of linearization of the circular episome. This linearized genome then can insert into the host genome, and if the break is at a point where the negative regulator E2 is disrupted, expression of the E6 and E7 oncogenes increases. The tumor suppressors p53 and Rb are degraded or inactivated, other biological events modulated by E6 and E7 occur, and the chances that the infected cell will divide inappropriately and will fail to undergo apoptosis increase (see (5, 30-33) for reviews). This clearly sets the stage for the development of cancer. It is likely that that the full development of the cancerous phenotype normally takes years to decades to develop, as most women are infected with the high-risk strains of HPV in their late teens and early twenties, and present with cancer in their late forties and early fifties.

This model, while sufficient to account for many, and perhaps most cases of cervical cancer, does not account for all, as some cervical cancer tumors provide evidence of an episomal, not an integrated form of HPV (34, 35), indicating that linearization and integration are not absolutely required.

Studies are ongoing regarding the importance of integration in HNC; it appears, as in the case of cervical cancer, that many but not all cases display integrated viral DNA ((36, 37) and references therein). Clearly, there are factors other than linearization and integration that can lead to the development of cancer. The known biological roles of E2, E6 and E7 strongly suggest that they are involved here as well.

Biomarker Studies Using Tissues as a Sample Source

The traditional way of screening for cervical cancer is with the Pap test. This procedure, which is recommended annually, has been credited with the vastly reduced number of cases of cervical cancer in countries where pap screening is routine as compared to countries where it is not routine. It has also been suggested that the presence of HPV could, and perhaps should, serve as a biomarker for cervical cancer (4).

More global approaches have also been considered; some have focused on directly examining changes in gene expression, while others have looked at changes in the methylation of promoter regions. For example, a study focused on examining changes in the transcriptome between HPV+ and HPV− head and neck tumors, as well as between HPV+ cervical and HPV+ HNC, found a number of differences in expression, such that HPV+ cervical and HNC had a significant up-regulation of cell-cycle genes as compared to the HPV− HNC (38). In fact, many of the up-regulated genes in HPV+ tissues were judged to be due to specific functions of E6 and E7. A number of additional studies have also undertaken gene expression profiling for HNC. Most did not differentiate between HPV+ and HPV− tumors (for example, (39-41)), though some have attempted to do so (38, 42). One outcome of this set of studies is an indication that while some potential biomarkers may be shared between HPV+ and HPV− tumors, others are specific for the HPV status of the tissue.

A number of studies have found that HNC and/or HPV infection can influence the methylation and therefore the expression of a number of cellular genes. In a paper published in 2005, Feng and coworkers (29) examined hypermethylation of 20 genes in patients with increasingly severe CIN and ICC. They found that the best panel of hypermethylated genes included DAPK1, RARB and TWIST1. Two years later, Henken et al (43) examined promoter methylation that occurred sequentially with progression of CIN and cervical cancer by looking at cells and cell lines that represented the various stages. This group found that a number of genes, many known to be involved in regulation of cell cycle, apoptosis and malignancy, appear to become sequentially methylated with progression of the disease. It is important to note, however, that this study was based on analysis of a number of isolated cell lines, and may or may not represent what happens in an individual tumor. In 2006, Worsham and coworkers analyzed the methylation of a panel of 35 genes with known associations to cancer using the methylation-specific multiplex ligation-dependent probe amplification (MS-MPLA) assay in six head and neck squamous cell carcinoma cell lines, and found that nine of these genes, TIMP3, APC, KLK10, TP73, CDH13, IGSF4, FRIT, ESR1 an DAPK1 were aberrantly methylated in at least some of the lines (44, 45). A year later, the same research group found that this same assay, now looking at actual patient tissues, found that a MS-MLPA assay for 22 different cancer genes in tissues obtained from HNC patients was able to identify several genes that were frequently hypermethylated, including RARB, APC and CHFR (46). These tissues were not analyzed for HPV sequences, but given that most were from smokers, it is likely that most were HPV negative. In a 2008 paper (47), another group of investigators utilized restriction landmark genomic scanning of 20 primary human cervical cancers to identify two novel genes, NOL4 and LHFPL4, which were methylated in 85% and 55% of the cancers examined, respectively, suggesting that they may be useful markers for cervical cancer screening. In another study, a differential methylation hybridization using a CpG island microarray was used to identify six genes (SOX1, PAX1, LMX1A, NKX6-1, WT1 and ONECUT1) as being more frequently methylated in squamous cell carcinomas than in normal controls (48).

Biomarker Studies Using Blood or Serum as a Sample Source

A team led by Dr. David Wong at UCLA has published a number of studies examining possible biomarkers for HNC; in one analysis, mRNA was extracted from the serum of patients and compared to that from healthy controls. Five transcripts, H3F3A, TPT1, FTH1, NCOA4 and ARCR, were identified as being significantly elevated in the patient sera (49). In this study, the samples were not sorted or differentiated on the basis of HPV status. Insulin-like Growth Factor-II (IGF-II) and IGF-Binding Protein 3 (IGF-BP3) have also been suggested as possible biomarkers for the early detection of cervical cancer (50), and it has been reported that the soluble α chain of the IL-15 receptor is associated with tumor progression in HNC (51).

Biomarker Studies Using Saliva as a Sample Source

The possibility of using saliva as a source of information regarding an individual's status has been the focus of intense interest, driven at least in part by the ease with which this material can be collected. In one recent study, a saliva-based protocol (based on the presence of antibodies) was shown to be able to function as well as blood-based protocols in determining the HIV status for pregnant women in rural India (52). A saliva-based diagnostic procedure to detect hepatitis infections, based on the presence of RNA, has been described (53), and a saliva-based test to search for the HER2 protein as a marker for breast cancer is under development (54). Interestingly, a small device called an IMPOD, or Integrated Microfluidic Platform for Oral Diagnostics, has been developed which is intended to test human saliva for evidence of periodontal disease; it measures levels of the collagen-cleaving enzyme matrix metalloproteinase-8 (MMP-8) in saliva (55). Recently, a group from the University of Southern California developed a protein map of human saliva, with 1166 unique proteins identified (56). Some studies have focused particularly on the usefulness of saliva in examining conditions in the head and neck area. For example, Sethi and coworkers reported at the 2008 AACR Annual Meeting that DNA extracted from 2 ml samples of saliva could be analyzed for alterations in gene copy number by multiplex ligation-dependent probe amplification (MLPA); this group found that gain of PMAIP1 and PTPN1 genes could separate HNACC patients from normal controls. These samples were not analyzed for the presence of HPV; nevertheless, this study provides proof of principle that DNA can be isolated from saliva and analyzed for markers of interest.

One very active laboratory in the area of saliva-based biomarkers for oral cancer is that of David Wong at UCLA. In one report (57), this lab was able to identify four genes, interleukin 1-beta (IL1B), ornithine decarboxylase antizyme 1 (OAZ), spermidine/spermine N1-acetyl transferase (SAT) and interleukin 8 (IL-8) that together, could identify saliva from cancer patients in nine out of ten samples from a group of 32 patients. In a report presented to the most recent Dental Society Conference, the Wong group reported that a two-lab biomarker study was able to verify that expression of a selection of genes, including IL-8, IL1B, H3F3A, OAZ1, S100P, SAT and DUSP1, were elevated in oral cancer samples. It should be noted that the sets of samples employed by this group was not sorted on the basis of HPV status, so it is unknown how many of them were HPV+, or if the predictive ability might be improved if HPV status were taken into consideration.

SUMMARY

The incidence and mortality of head and neck cancers caused by high risk types of human papillomaviruses is increasing and there is currently no good way to screen for early stages of this condition. The idea behind the present invention is that as the development of HPV-associated head and neck cancers proceed, a number of viral and cellular events occur that can be exploited as biomarkers. This combination of biomarkers creates a molecular signature for cells transformed by HPV that can be used to identify individuals likely to develop cancer. Furthermore, due to the anatomical location of these tumors, cells from these cancers can be found in saliva in sufficient numbers for the detection of these biomarkers. Accordingly, one object of the present invention is to provide a rapid accurate and cost-effective diagnostic tool for the early identification of pre-cancerous and cancerous lesions in the head and neck area using saliva as a sample source.

In particular, one embodiment of the present invention provides a method that detects a series of biomarkers that can distinguish between a non-diseased condition and a situation where the patient is likely to develop or has HPV-associated head and neck cancer. In one embodiment, the method detects increases/decreases in biomarker gene expression. In another embodiment, the method detects changes in specific DNA methylation patterns. The technology can be adapted to high-throughput, clinically compatible applications where a plurality of HPV and HNC-associated host cell biomarkers are simultaneously detected from a single sample.

In one embodiment, the method comprises, first, obtaining a biological sample from a patient, such as for example, a tissue, plasma and/or saliva sample. In preferred embodiments, the samples are processed to isolate DNA and/or RNA. The biological sample(s) are then subjected to screening for the presence or absence of the biomarker.

One embodiment of the present invention provides a method of detecting biomarkers associated with head and neck tumors in a subject. The first step of the method comprises contacting a first biological sample from the subject, wherein the first biological sample is selected from the group consisting of saliva, whole blood, white blood cells, serum, plasma and biopsy tissue from the throat, oropharynx or mouth, with: (1) a first reagent that specifically binds to one or more than one human papillomavirus (HPV) biomarker; and (2) a second reagent that specifically binds to one or more than one host cell biomarker, wherein the host cell biomarker is differentially expressed in head and neck tumor cells as compared to normal cells. The next steps of the method comprise detecting the presence or absence of the HPV marker; and determining whether or not the host cell marker is differentially expressed in the biological sample. In one embodiment, differential expression of the host cell marker is accomplished by comparing the expression level of the host cell marker in the biological sample to the expression level of the same host cell marker for at least one reference sample, where the reference sample is a comparable biological sample obtained from a disease-free subject.

In one embodiment of the method the first reagent is an oligonucleotide and the HPV biomarker is a HPV-specific nucleic acid. In one embodiment, the oligonucleotide reagent can comprise at least 15 nucleotides. For example, each oligonucleotide can comprise at least 20, 25, 50, 75, 100, 125, 150, 200, 225, 250, 275, 300, 325, 350, 400 or more nucleotides. In preferred embodiments the HPV biomarker is a HPV mRNA or a complement thereof. In a preferred method, the biomarker is an mRNA encoded by an HPV gene, such as E2, E5, E6, E6* or E7. The preferred method may further entail identifying splice variants of the HPV gene(s). In particularly preferred embodiments, the HPV mRNA is selected from the group consisting of E2 mRNA, E6 mRNA and E7 mRNA.

In another embodiment the first reagent is an antibody and the HPV biomarker is a HPV polypeptide. Conversely, in another embodiment the first reagent can be an HPV antigen and the HPV biomarker can be an anti-HPV antibody.

In preferred embodiments the first reagent specifically binds to a plurality of HPV biomarkers and/or the second reagent specifically binds to a plurality of host cell biomarkers. For example, one, two, three, four, five, six, seven, eight, nine, ten, eleven, twelve, thirteen, fourteen, fifteen, sixteen, seventeen, eighteen, nineteen or more host cell biomarkers can be selected from a group of biomarkers differentially expressed in HNC cells, such as H3F3A, TPT1, FTH1, NCOA4, ARCR, IGF-II, IGF-BP3, soluble a chain of the IL-15 receptor, IL1B, OAZ1, SAT, IL-8, S100P, DUSP1, LAMC2, COL4A1, COL1A1, PADI1, HA3 and CD44.

In another preferred embodiment one, two, three, four, five, six, seven, eight, nine, ten, eleven, twelve, thirteen, fourteen, fifteen, sixteen, seventeen, eighteen, nineteen, twenty, twenty-five, thirty, forty, fifty or more host cell biomarkers can be selected from a group of biomarkers differentially expressed in HPV positive HNC cells, such as AL833646, BF055370, BUB1B, CCDC5, CCNA1, CCNB1, CCND1, CCND2, CCNE2, CDC2, CDC7, CDK2, CDKN2A, CDKN2B, CDKN2C, CENPF, CHEK1, E2F2, E2F3, E2F7, EHHADH, EREG, FKSG14, 10 FLJ31952, FLJ37881, FLJ39749, FLJ42662, FLJ4628, GADD45G, GAS1, HCAP-G, KIF2C, KIRREL, KLK10, KNTC1, MCM2, MCM3, MCM6, MCM7, MCM8, MCM10, MGC24665, MTB, MYNN, NAP1L2, NR1D2, ORC1L, ORC3L, PARC, PCNA, RFC4, RIBC2, RPA2, SESN3, SMC2L1, SMC4L1, STAG3, SYCP2, SYNGR3, TAF7L, TCAM1, TFDP1 and TP53.

In preferred embodiments, the second reagent is an oligonucleotide and the host cell biomarker is a nucleic acid. In one embodiment, the oligonucleotide reagent can comprise at least 15 nucleotides. For example, each oligonucleotide can comprise at least 20, 25, 50, 75, 100, 125, 150, 200, 225, 250, 275, 300, 325, 350, 400 or more nucleotides. In preferred embodiments, the host cell biomarker is a host cell mRNA or a complement thereof.

In another embodiment, the HPV biomarker or the host cell biomarker is DNA. In a preferred embodiment the DNA is a CpG containing promoter and the method further comprises determining whether or not the CpG-containing promoter is aberrantly methylated. In a preferred embodiment, the differential methylation of one, two, three, four or more HPV genes, e.g. the E2, E5, E6 or E7 promoter, is determined. In one embodiment whether or not the CpG-containing promoter is aberrantly methylated is determined by comparing the methylation of the CpG-containing promoter in the biological sample to the methylation of the CpG-containing promoter for at least one reference sample, where the reference sample is a comparable biological sample obtained from a disease-free subject. In another embodiment, one, two, three, four, five, six, seven, eight, nine, ten, eleven, twelve, thirteen, fourteen, fifteen, sixteen, seventeen, eighteen, nineteen or more CpG containing promoters, such as the host cell promoters for DAPK1, RARB, TWIST1, TIMP3, APC, KLK10, TP73, CDH13, IGSF4, FHIT, ESR1, CHFR, NOL4, LHFPL4, SOX1, PAX1, LMX1A, NKX6-1, WT-1 and ONE-CUT1, are selected for analysis.

In another embodiment the HPV biomarker is DNA and the method further comprises distinguishing between a high risk strain of HPV and a low risk strain of HPV. In a preferred embodiment, the method further comprises identifying HPV16 DNA or HPV18 DNA. In another embodiment, the integration of HPV DNA in the host genome is determined.

In one embodiment the method further comprises comparing the expression level of the host cell marker in the biological sample to the expression level of the same host cell marker for one or more than one additional reference sample, where the reference sample is a comparable biological sample obtained from a patient with an HPV positive head and neck tumor or a patient with an HPV negative head and neck tumor.

In one embodiment of the present invention the first biological sample is compared to a second biological sample from the subject. Preferably, the first biological sample is saliva and the second biological sample is whole blood, blood cells, serum, plasma, or a tissue sample from the throat, oropharynx or mouth. For comparison, the method further comprises the additional steps of contacting the second biological sample from the subject with; (1) a reagent that specifically binds to a HPV biomarker, and (2) a reagent that specifically binds to a host cell marker differentially expressed or in head and neck tumor cells as compared to normal cells. The next steps are detecting the presence or absence of the HPV marker; and determining whether or not the host cell marker is differentially expressed in the first sample and/or the second sample.

BRIEF DESCRIPTION OF THE DRAWINGS

These and other features, aspects and advantages of the present invention will become better understood with regard to the following description, appended claims, and accompanying figures where:

FIG. 1 shows PCR amplification with DNA-specific and RNA-specific primers.

FIG. 2 shows analysis of the differentially methylated pTOPO plasmid containing the CDK2B promoter region. FIGS. 2B and 2C show methylated DNA, either undigested (FIG. 2B) or digested with HhaI (FIG. 2C); FIGS. 2D and 2E show unmethylated DNA, either undigested (FIG. 2D) or digested with HhaI (FIG. 2E). The peaks remaining in FIG. 2E show the DNA ladder.

DETAILED DESCRIPTION OF THE INVENTION

Figure 1A:
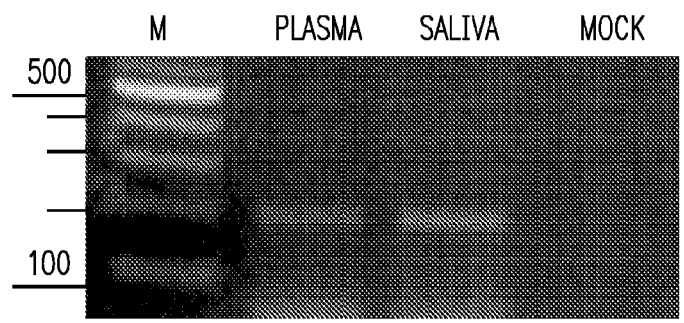
FIG. 1A shows PCR amplification results when nucleic acids from 0.280 ml of plasma and saliva were isolated using the QIAamp kit (Qiagen) and eluted into 40 µl of water. One µl of purified sample was used for PCR amplification of SRF6 for 39 cycles using genomic DNA specific primers.

Generally, the methods of this invention find particular use in diagnosing or providing a prognosis for head and neck cancer (HNC) by detecting human papilloma virus (HPV) markers and host cell markers, which are differentially expressed (down or upregulated) in HNC tumor cells. These markers can thus be used diagnostically to distinguish HPV+ HNC from HPV− HNC or normal cells. The markers can be used alone or in combination. According to one embodiment of the present invention, there is provided a method for the detection of changes in expression levels of selected viral and cellular genes or biomarkers. Another embodiment of the present invention provides a method for detecting changes in the methylation status of their promoters in tissues, blood/serum and saliva. Several sets of matched samples can be used to identify biomarkers that can be found in saliva and have the ability to distinguish between HPV-associated head and neck cancer and controls. The methods provide a rapid, accurate and cost-effective diagnostic tool for the early identification of pre-cancerous and cancerous lesions in the head and neck area, using saliva as a sample source.

DEFINITIONS

The term head and neck cancer (HNC) refers to a group of biologically similar cancers originating from the upper aerodigestive tract, including the lip, oral cavity (mouth), nasal cavity, paranasal sinuses, pharynx, and larynx. Most head and neck cancers are squamous cell carcinomas, originating from the mucosal lining (epithelium) of these regions.

Human papillomavirus (HPV), in particular HPV16, is a suggested causal factor for head and neck squamous cell carcinoma (HNSCC). Approximately 15 to 25% of HNSCC contain genomic DNA from HPV, and the association varies based on the site of the tumor, especially in the oropharynx, with highest distribution in the tonsils, where HPV DNA is found in (45 to 67%) of the cases, less often in the hypopharynx (13%-25%), and least often in the oral cavity (12%-18%) and larynx (3%-7%).

The term "marker" or "biomarker" refers to a molecule (typically protein, nucleic acid, carbohydrate, or lipid) that is expressed in the cell, expressed on the surface of a cancer cell, secreted by a cancer cell or modified in a cancer cell in comparison to a normal cell, and which is useful for the diagnosis of cancer, for providing a prognosis, and for preferential targeting of a pharmacological agent to the cancer cell. Oftentimes, such markers are molecules that are differentially expressed, e.g., overexpressed or underexpressed in a HPV+ HNC cell in comparison to a normal cell, for instance, 1-fold over/under expression, 2-fold over/under expression, 3-fold over/under expression or more in comparison to a normal cell, a HPV− HNC cell or a HPV+ cervical cancer cell. Further, a marker can be a molecule that is inappropriately synthesized in the cancer cell, for instance, a molecule that contains deletions, additions or mutations in comparison to the molecule expressed on a normal cell.

Accession numbers for nucleic acid and protein sequences of representative biomarkers, which may be differentially expressed in HNC cells, include the following:

TABLE 1

| Biomarker | Name | Genbank Accession Number(s) |
|---|---|---|
| H3F3A | H3 histone, family 3A | NM_002107, BC029405, AK293541 |
| TPT1 | tumor protein, translationally-controlled 1 | NM_003295, X16064, AK296587 |
| FTH1 | ferritin, heavy polypeptide 1 | NM_002032, AB062402 |
| NCOA4 | nuclear receptor coactivator 4 | NM_005437, NM_001145260, NM_01145261, NM_01145262, NM_01145263, L49399 |
| ARCR (aka RHOA) | ras homolog gene family, member A | NM_001664, BC001360 |
| IGF-II (IGF2) | insulin-like growth factor 2 | NM_001127598, NM_000612, NM_001007139 |
| IGF-BP3 | insulin-like growth factor binding protein 3 | NM_001013398, NM_006547 |
| IL15RA | interleukin 15 receptor, alpha | NM_172200, NM_002189 |
| IL1B | interleukin 1, beta | NM_000576, M15330, AB451494 |
| OAZ1 | ornithine decarboxylase antizyme 1 | NM_004152 |
| SAT1 | spermidine/spermine N1-acetyltransferase 1 | NM_002970, M55580, AF25129 |
| IL-8 | interleukin 8 | NM_000584, Y00787 |
| S100P | S100 calcium binding protein P | NM_005980, X65614 |
| DUSP1 | dual specificity phosphatase 1 | NM_004417, X68277, AK298047 |
| LAMC2 | laminin, gamma 2 | NM_005562, NM_018891, Z15008 |
| COL4A1 | collagen, type IV, alpha 1 | NM_001845, J04217 |
| COL1A1 | collagen, type I, alpha 1 | NM_000088, Z74615 |
| PADI1 | peptidyl arginine deiminase, type I | NM_013358, AB033768, AK293275 |
| HA3 (aka AKAP13) | A kinase (PRKA) anchor protein 13 | NM_007200, NM_006738, NM_144767, M90360 |
| CD44 | CD44 molecule (Indian blood group) | NM_000610, NM_001001389, NM_001001390, NM_001001391, NM_001001392, M59040 |

Accession numbers for nucleic acid and protein sequences of representative biomarkers, which may be differentially expressed in HPV+ HNC cells, include the following:

TABLE 2

| Biomarker | Name | Genbank Accession Number(s) |
|---|---|---|
| AL833646 | unknown protein | AL833646 |
| BF055370 | unknown protein | BF055370 |
| BUB1B | budding uninhibited by benzimidazoles 1 homolog beta (yeast)/mitotic checkpoint protein kinase BUB1B | NM_001211, AF107297 |
| CCDC5 | coiled-coil domain containing 5 (spindle associated) | BC005958, BC014003 |
| CCNA1 | cyclin A1 | NM_003914, U66838 |
| CCNB1 | cyclin B1 | NM_031966, U22364 |
| CCND1 | cyclin D1 | NM_053056 NM_001758, Z23022 |
| CCND2 | cyclin D2 | NM_001759, AF518005 |
| CCNE2 | cyclin E2 | NM_057749, AF091433 |
| CDC2 | cell division cycle 2, G1 to S and G2 to M | NM_001786, BC014563 |
| CDC7 | cell division cycle 7 homolog (S. cerevisiae) | NM_003503, AF015592 |
| CDK2 | cyclin-dependent kinase 2 | NM_052827, M68520 |
| CDKN2A | cyclin-dependent kinase inhibitor 2A | NM_000077 |
| CDKN2C | cyclin-dependent kinase inhibitor 2C (p18, inhibits CDK4) | NM_001262, XM_932741, XM_945305, BC000598 |
| CENPF | centromere protein F, 350/400ka (mitosin) | NM_016343, NM_005196, U30872 |
| CHEK1 | CHK1 checkpoint homolog (S. pombe) | NM_001274, AF016582, BC017575 |
| E2F2 | E2F transcription factor 2 | NM_004091, L22846 |
| E2F3 | E2F transcription factor 3 | NM_001949, Y10479 |
| E2F7 | E2F transcription factor 7 | XM_084871, BC016658 |
| EHHADH | enoyl-Coenzyme A, hydratase/3-hydroxyacyl Coenzyme A dehydrogenase | L07077 |
| EREG | Epiregulin | D30783 |
| FKSG14 | centromere protein K | NM_022145, BC008504 |
| 10 FLJ31952 | unknown protein | AK056514 |
| FLJ37881 | unknown protein | AK095200 |
| FLJ39749 | unknown protein | AK097068 |
| FLJ42662 | unknown protein | AK124653 |
| FLJ4628 | unknown protein | (not found) |
| GADD45G | growth arrest and DNA-damage-inducible, gamma | NM_006705, D83023 |
| GAS1 | growth arrest-specific 1 | NM_002048 |
| HCAP-G | non-SMC condensin I complex, subunit G | NM_022346, AF331796 |
| KIF2C | kinesin family member 2C | NM_006845, U63743 |
| KIRREL | kin of IRRE like (Drosophila) | NM_018240, AK001707 |
| KLK10 | kallikrein-related peptidase 10 | NM_002776, AF024605 S82666 |
| KNTC1 | kinetochore associated 1 | NM_014708 |
| MCM2 | minichromosome maintenance complex component 2 | NM_004526, X67334 |

TABLE 2-continued

| Biomarker | Name | Genbank Accession Number(s) |
|---|---|---|
| MCM3 | minichromosome maintenance complex component 3 | X62153 |
| MCM6 | minichromosome maintenance complex component 6 | NM_005915 |
| MCM7 | minichromosome maintenance complex component 7 | NM_005916 |
| MCM8 | minichromosome maintenance complex component 8 | NM_032485, AJ439063 |
| MCM10 | minichromosome maintenance complex component 10 | NM_182751, AB042719 |
| MGC24665 | chromosome 16 open reading frame 75 | NM_152308 |
| MTB aka NCAPG2 | non-SMC condensin II complex, subunit G2 | NM_017760, BC043404 |
| MYNN | Myoneurin | AF148848 |
| NAP1L2 | nucleosome assembly protein 1-like 2 | NM_021963, AF136178 |
| NR1D2 | nuclear receptor subfamily 1, group D, member 2 | BC045613 |
| ORC1L | origin recognition complex, subunit 1-like (yeast) | NM_004153 |
| ORC3L | origin recognition complex, subunit 3-like (yeast) | NM_181837, AF093535 |
| PARC | p53-associated parkin-like cytoplasmic protein | AY145132 |
| PCNA | proliferating cell nuclear antigen | NM_182649, J04718 |
| RFC4 | replication factor C (activator 1) 4, 37 kDa | NM_002916 |
| RIBC2 | RIB43A domain with coiled-coils 2 | NM_015653, AK098586 |
| RPA2 | replication protein A2, 32 kDa | BC021257 |
| SESN3 | sestrin 3 | NM_144665, AK096300 |
| SMC2L1 | structural maintenance of chromosomes 2 | NM_006444, AF092563 |
| SMC4L1 | structural maintenance of chromosomes 4 | NM_005496, NM_001002800, AK225437 |
| SYCP2 | synaptonemal complex protein 2 | NM_014258, Y08982 |
| SYNGR3 | synaptogyrin 3 | AJ002309 |
| TAF7L | TAF7-like RNA polymerase II, TATA box binding protein (TBP)-associated factor, 50 kDa | AF285595 |
| TCAM1 | testicular cell adhesion molecule 1 homolog (mouse) | AB026156 |
| TFDP1 | transcription factor Dp-1 | NM_007111, BC011685 |
| TP53 | tumor protein p53 | NM_000546, AF307851 |

The nucleotide and amino acid sequences corresponding to the forgoing Accession Numbers are incorporated herein by reference.

It will be understood by the skilled artisan that markers may be used singly or in combination with other markers for any of the uses, e.g., the diagnosis or prognosis of HPV+ HNC, disclosed herein.

"Biological sample" includes sections of tissues such as biopsy and autopsy samples, and frozen sections taken for histologic purposes. Such samples include whole blood and blood fractions or products (e.g., serum, plasma, white blood cells, and the like), sputum, saliva, lymph and tongue tissue, cultured cells, e.g., primary cultures, explants, and transformed cells, etc. The biological sample is typically obtained from a eukaryotic organism, preferably a mammal, most preferably a primate, e.g., a human subject.

A "biopsy" refers to the process of removing a tissue sample for diagnostic or prognostic evaluation, and to the tissue specimen itself. Any biopsy technique known in the art can be applied to the diagnostic and prognostic methods of the present invention. The biopsy technique applied will depend on the location of the tissue to be evaluated (e.g the lip, oral cavity, nasal cavity, paranasal sinuses, pharynx, larynx, etc.) and the size of the tumor, among other factors. Representative biopsy techniques include, but are not limited to, excisional biopsy, incisional biopsy, needle biopsy, and surgical biopsy. An "excisional biopsy" refers to the removal of an entire tumor mass with a small margin of normal tissue surrounding it. An "incisional biopsy" refers to the removal of a wedge of tissue that includes a cross-sectional diameter of the tumor. A diagnosis or prognosis made by endoscopy or fluoroscopy can require a "core-needle biopsy" of the tumor mass, or a "fine-needle aspiration biopsy" which generally obtains a suspension of cells from within the tumor mass. Biopsy techniques are discussed, for example, in *Harrison's Principles of Internal Medicine*, Kasper, et al., eds., 16th ed., 2005, Chapter 70, and throughout Part V.

The terms "overexpress," "overexpression" or "overexpressed" interchangeably refer to a protein or nucleic acid (RNA) that is transcribed or translated at a detectably greater level, usually in a cancer cell, in comparison to a normal cell. The term includes overexpression due to transcription, post transcriptional processing, translation, post-translational processing, cellular localization (e.g., organelle, cytoplasm, nucleus, cell surface), and RNA and protein stability, as compared to a normal cell. Overexpression can be detected using conventional techniques for detecting mRNA (i.e., RT-PCR, PCR, hybridization) or proteins (i.e., ELISA, immunohistochemical techniques). Overexpression can be 10%, 20%, 30%, 40%, 50%, 60%, 70%, 80%, 90% or more in comparison to a normal cell. In certain instances, overexpression is 1-fold, 2-fold, 3-fold, 4-fold or more higher levels of transcription or translation in comparison to a normal cell.

The terms "underexpress," "underexpression" or "underexpressed" interchangeably refer to a protein or nucleic acid (RNA) that is transcribed or translated at a detectably lower level, usually in a cancer cell, in comparison to a normal cell. The term includes underxpression due to transcription, post transcriptional processing, translation, post-translational processing, cellular localization (e.g., organelle, cytoplasm, nucleus, cell surface), and RNA and protein stability, as compared to a normal cell. Underexpression can be detected using conventional techniques for detecting mRNA (i.e., RT-PCR, PCR, hybridization) or proteins (i.e., ELISA, immunohistochemical techniques). Underexpression can be 10%, 20%, 30%, 40%, 50%, 60%, 70%, 80%, 90% etc. in comparison to a normal cell. In certain instances, underexpression is 1-fold, 2-fold, 3-fold, 4-fold or more lower levels of transcription or translation in comparison to a normal cell.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1987-2005, Wiley Interscience)).

A preferred example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, Proc. Natl. Acad. Sci. USA 89:10915 (1989)) alignments (B) of 50, expectation (E) of 10, M=5, N=−4, and a comparison of both strands.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

A particular nucleic acid sequence also implicitly encompasses "splice variants" and nucleic acid sequences encoding truncated forms of cancer antigens. Similarly, a particular protein encoded by a nucleic acid implicitly encompasses any protein encoded by a splice variant or truncated form of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition. Nucleic acids can be truncated at the 5' end or at the 3' end. Polypeptides can be truncated at the N-terminal end or the C-terminal end. Truncated versions of nucleic acid or polypeptide sequences can be naturally occurring or recombinantly created.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M). See, e.g., Creighton, *Proteins* (1984).

A "label" or a "detectable moiety" is a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$, is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al., supra.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min, an annealing phase lasting 30 sec.-2 min, and an extension phase of about 72° C. for 1-2 min. Protocols and guidelines for low and high stringency amplification reactions are provided, e.g., in Innis et al. (1990) *PCR Protocols, A Guide to Methods and Applications*, Academic Press, Inc. N.Y.).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding. Antibodies can be polyclonal or monoclonal, derived from serum, a hybridoma or recombinantly cloned, and can also be chimeric, primatized, or humanized.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce $F(ab)'_2$, a dimer of Fab which itself is a light chain joined to $V_H$-$C_H$1 by a disulfide bond. The $F(ab)'_2$ may be reduced under mild conditions to break the disulfide linkage in the hinge region, thereby converting the $F(ab)'_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

Biomarker Panels

Certain embodiments of the present invention provide methods to qualitatively and/or quantitatively analyze a panel of candidate biomarkers. In particular, matched sample sets of HPV+ and HPV− tonsillar tissue, blood and saliva can be analyzed for the presence of HPV DNA sequences, the presence and levels of HPV-encoded mRNA and proteins, changes in the expression of host-encoded biomarkers, and the methylation status of selected host and viral promoters. The most suitable biomarkers will correlate with HPV and cancer status. In one embodiment of the present invention matched sets of samples that include cancer tissue, adjacent normal tissue, blood samples and saliva samples are obtained from the same patient, which may contain both HPV positive and HPV negative lesions. Screening the panel for HPV biomarkers will specifically and sensitively identify HPV-positive malignancies. Saliva collected from individuals known to have HPV+ head and neck cancer can serve as a positive control.

A number of global-based screens have been utilized in efforts to identify panels of either proteins, messages, or methylated promoters that can be used in screening protocols for either HNC in general or for HPV-associated cancers. However, these individual studies have identified potential panels that are largely non-overlapping with each other, and have not incorporated these sets of biomarkers into a meaningful, consistent and robust panel. Furthermore, to our knowledge, none of these screening protocols have focused on detecting either message or proteins from the HPV virus itself. Given that at least three of these viral messages/proteins, E2, E6 and E7, are known to have biological activities that contribute to (E6 and E7) or reduce (E2) the development of cancer, their inclusion into a screening strategy adds value to whatever screening protocols are ultimately employed. Finally, most of the studies to date have used actual tissues for samples, a source that unlikely to be practical for the development of widespread screening.

Various embodiments of the present invention detect and compare one or more of three sets of phenomena—the presence of HPV DNA, the presence of altered levels of cellular and viral messages, and alterations in methylation patterns for cellular and viral genes. Another embodiment of the present invention detects and compares these biomarkers in one or more of three types of material—tissue, blood and saliva. In preferred embodiments a panel of biomarkers are selected, which are measurable in saliva. For cellular mRNA expression levels and DNA methylation, biomarkers will be selected from previously published global analyses, while for the viral mRNA expression levels and methylation, the biomarkers are selected on the basis of what is known regarding the molecular activities of the virus and its proteins.

The nucleic acids encoding biomarkers or their encoded polypeptides refer to all forms of nucleic acids (e.g., gene, pre-mRNA, mRNA) or proteins, their polymorphic variants, alleles, mutants, and interspecies homologs that (as applicable to nucleic acid or protein): (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of at least about 25, 50, 100, 200, 500, 1000, or more amino acids, to a polypeptide encoded by a referenced nucleic acid or an amino acid sequence described herein; (2) specifically bind to antibodies, e.g., polyclonal antibodies, raised against an immunogen comprising a referenced amino acid sequence, immunogenic fragments thereof, and conservatively modified variants thereof; (3) specifically hybridize under stringent hybridization conditions to a nucleic acid encoding a referenced amino acid sequence, and conservatively modified variants thereof; (4) have a nucleic acid sequence that has greater than about 95%, preferably greater than about 96%, 97%, 98%, 99%, or higher nucleotide sequence identity, preferably over a region of at least about 25, 50, 100, 200, 500, 1000, or more nucleotides, to a reference nucleic acid sequence. A polynucleotide or polypeptide sequence is typically from a mammal including, but not limited to, primate, e.g., human; rodent, e.g., rat, mouse, hamster; cow, pig, horse, sheep, or any mammal. The nucleic acids and proteins of the invention include both naturally occurring or recombinant molecules. Truncated and alternatively spliced forms of these antigens are included in the definition.

The phrase "specifically (or selectively) binds" when referring to a protein, nucleic acid, antibody, or small molecule compound refers to a binding reaction that is determinative of the presence of the protein or nucleic acid, often in a heterogeneous population of proteins or nucleic acids and other biologics. In the case of nucleic acids, an oligonucleotide, polynucleotide or nucleic acid specifically binds to a particular nucleic acid biomarker under stringent hybridization conditions. In the case of antibodies, under designated immunoassay conditions, a specified antibody may bind to a particular protein at least two times the background and more typically more than 10 to 100 times background. Specific binding to an antibody under such conditions requires an antibody that is selected for its specificity for a particular protein. For example, polyclonal antibodies can be selected to obtain only those polyclonal antibodies that are specifically immunoreactive with the selected antigen and not with other proteins. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988) for a description of immunoassay formats and conditions that can be used to determine specific immunoreactivity).

Diagnostic and Prognostic Methods

The present invention provides methods of diagnosing or providing prognosis of head and neck cancer (HNC) by detecting the expression of markers differentially expressed in HNC cells. Diagnosis involves determining the level of a HPV or host cell polypeptide or nucleic acid in a patient or patient sample and then comparing the level to a baseline or range. Typically, the baseline value is representative of levels of the polypeptide or nucleic acid in a healthy person not suffering from HNC, as measured using a biological sample, such as a tissue biopsy, blood or saliva. Variation of levels of a polypeptide or nucleic acid of the invention from the baseline range (either up or down) indicates that the patient has a cancer or is at risk of developing a cancer, depending on the marker used.

As used herein, the term "providing a prognosis" refers to providing a prediction of the probable course and outcome of HNC. The methods can also be used to devise a suitable therapy for HNC treatment, e.g., by indicating whether or not the HNC tumor is still at a benign stage or if the HNC tumor had advanced to a stage where aggressive therapy would be ineffective.

Nucleic acid binding molecules such as probes, oligonucleotides, oligonucleotide arrays, and primers can be used in assays to detect differential RNA expression in patient samples, e.g., RT-PCR. In one embodiment, RT-PCR is used according to standard methods known in the art. In another embodiment, PCR assays such as Taqman° assays available from, e.g., Applied Biosystems, can be used to detect nucleic acids and variants thereof. In other embodiments, qPCR and nucleic acid microarrays can be used to detect nucleic acids. Reagents that bind to selected cancer biomarkers can be prepared according to methods known to those of skill in the art or purchased commercially.

Analysis of nucleic acids can be achieved using routine techniques such as Southern analysis, reverse-transcriptase polymerase chain reaction (RT-PCR), or any other methods based on hybridization to a nucleic acid sequence that is complementary to a portion of the marker coding sequence (e.g., slot blot hybridization) are also within the scope of the present invention. Applicable PCR amplification techniques are described in, e.g., Ausubel et al. and Innis et al., supra. General nucleic acid hybridization methods are described in Anderson, "Nucleic Acid Hybridization," BIOS Scientific Publishers, 1999. Amplification or hybridization of a plurality of nucleic acid sequences (e.g., genomic DNA, mRNA or cDNA) can also be performed from mRNA or cDNA sequences arranged in a microarray. Microarray methods are generally described in Hardiman, "Microarrays Methods and Applications: Nuts & Bolts," DNA Press, 2003; and Baldi et al., "DNA Microarrays and Gene Expression: From Experiments to Data Analysis and Modeling," Cambridge University Press, 2002.

Analysis of nucleic acid markers and their variants can be performed using techniques known in the art including, without limitation, microarrays, polymerase chain reaction (PCR)-based analysis, sequence analysis, and electrophoretic analysis. A non-limiting example of a PCR-based analysis includes a Taqman® allelic discrimination assay available from Applied Biosystems. Non-limiting examples of sequence analysis include Maxam-Gilbert sequencing, Sanger sequencing, capillary array DNA sequencing, thermal cycle sequencing (Sears et al., *Biotechniques*, 13:626-633 (1992)), solid-phase sequencing (Zimmerman et al., *Methods Mol. Cell. Biol.*, 3:39-42 (1992)), sequencing with mass spectrometry such as matrix-assisted laser desorption/ionization time-of-flight mass spectrometry (MALDI-TOF/MS; Fu et al., *Nat. Biotechnol.*, 16:381-384 (1998)), and sequencing by hybridization. Chee et al., *Science,* 274:610-614 (1996); Drmanac et al., *Science,* 260:1649-1652 (1993); Drmanac et al., *Nat. Biotechnol.*, 16:54-58 (1998). Non-limiting examples of electrophoretic analysis include slab gel electrophoresis such as agarose or polyacrylamide gel electrophoresis, capillary electrophoresis, and denaturing gradient gel electrophoresis. Other methods for detecting nucleic acid variants include, e.g., the INVADER® assay from Third Wave Technologies, Inc., restriction fragment length polymorphism (RFLP) analysis, allele-specific oligonucleotide hybridization, a heteroduplex mobility assay, single strand conformational polymorphism (SSCP) analysis, single-nucleotide primer extension (SNUPE) and pyrosequencing.

Alternatively, antibody reagents can be used in assays to detect expression levels of HPV of host cell polypeptides in patient samples using any of a number of immunoassays known to those skilled in the art Immunoassay techniques and protocols are generally described in Price and Newman, "Principles and Practice of Immunoassay," 2nd Edition, Grove's Dictionaries, 1997; and Gosling, "Immunoassays: A Practical Approach," Oxford University Press, 2000. A variety of immunoassay techniques, including competitive and non-competitive immunoassays, can be used. See, e.g., Self et al., *Curr. Opin. Biotechnol.,* 7:60-65 (1996). The term immunoassay encompasses techniques including, without limitation, enzyme immunoassays (EIA) such as enzyme multiplied immunoassay technique (EMIT), enzyme-linked immunosorbent assay (ELISA), IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated Immunoassays can also be used in conjunction with laser induced fluorescence. See, e.g., Schmalzing et al., *Electrophoresis,* 18:2184-93 (1997); Bao, *J. Chromatogr. B. Biomed. Sci.*, 699:463-80 (1997). Liposome immunoassays, such as flow-injection liposome immunoassays and liposome immunosensors, are also suitable for use in the present invention. See, e.g., Rongen et al., *J. Immunol. Methods,* 204:105-133 (1997). In addition, nephelometry assays, in which the formation of protein/antibody complexes results in increased light scatter that is converted to a peak rate signal as a function of the marker concentration, are suitable for use in the methods of the present invention. Nephelometry assays are commercially available from Beckman Coulter (Brea, Calif.; Kit #449430) and can be performed using a Behring Nephelometer Analyzer (Fink et al., *J. Clin. Chem. Clin. Biochem.,* 27:261-276 (1989)).

Specific immunological binding of the antibody to antigens can be detected directly or indirectly. Direct labels include fluorescent or luminescent tags, metals, dyes, radionuclides, and the like, attached to the antibody. An antibody labeled with iodine-125 ($^{125}$I) can be used. A chemiluminescence assay using a chemiluminescent antibody specific for the nucleic acid is suitable for sensitive, non-radioactive detection of protein levels. An antibody labeled with fluorochrome is also suitable. Examples of fluorochromes include, without limitation, DAPI, fluorescein, Hoechst 33258, R-phycocyanin, B-phycoerythrin, R-phycoerythrin, rhodamine, Texas red, and lissamine Indirect labels include various enzymes well known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A detectable moiety can be used in the assays described herein. A wide variety of detectable moieties can be used, with the choice of label depending on the sensitivity required, ease of conjugation with the antibody, stability requirements, and available instrumentation and disposal provisions. Suitable detectable moieties include, but are not limited to, radionuclides, fluorescent dyes (e.g., fluorescein, fluorescein isothiocyanate (FITC), Oregon Green™, rhodamine, Texas red, tetrarhodimine isothiocyanate (TRITC), Cy3, Cy5, etc.), fluorescent markers (e.g., green fluorescent protein (GFP), phycoerythrin, etc.), autoquenched fluorescent compounds that are activated by tumor-associated proteases, enzymes (e.g., luciferase, horseradish peroxidase, alkaline phosphatase, etc.), nanoparticles, biotin, digoxigenin, and the like.

Useful physical formats comprise surfaces having a plurality of discrete, addressable locations for the detection of a plurality of different markers. Such formats include microarrays and certain capillary devices. See, e.g., Ng et al., *J. Cell Mol. Med.,* 6:329-340 (2002); U.S. Pat. No. 6,019,944. In these embodiments, each discrete surface location may comprise antibodies to immobilize one or more markers for detection at each location. Surfaces may alternatively comprise one or more discrete particles (e.g., microparticles or nanoparticles) immobilized at discrete locations of a surface, where the microparticles comprise antibodies to immobilize one or more markers for detection.

Analysis can be carried out in a variety of physical formats. For example, the use of microtiter plates or automation could be used to facilitate the processing of large numbers of test samples. Alternatively, single sample formats could be developed to facilitate diagnosis or prognosis in a timely fashion.

Alternatively, the antibodies or nucleic acid probes of the invention can be applied to sections of patient biopsies immobilized on microscope slides. The resulting antibody staining or in situ hybridization pattern can be visualized using any one of a variety of light or fluorescent microscopic methods known in the art.

In one embodiment of the present invention, the panel is used to test several matched sets of patient samples—tissue, blood and saliva. This screen will confirm which of the biomarkers are most meaningful, consistent, and not due to random chance. This further streamlined panel may then be utilized on a population of saliva samples, using saliva from known HPV+ HNC patients as a positive control. Our overall objective is to provide a panel of measurements that can be made using an easily-obtained material such as saliva that will accurately predict the development of HNC in human patients.

Preparation and Analysis of Samples

Tumor tissues can be obtained as surgical specimens. Matching sets of adjacent normal tissue, blood and saliva from the same patient may also provided. These samples can be processed for the analysis of DNA sequences, methylation status, the presence of viral and cellular RNA, and the presence of specific proteins using standard procedures. The basic methods regarding the extraction and processing of DNA and RNA from tissues and blood are well-established. In addition, formalin-fixed, paraffin-embedded tissues may be employed by using commercially available kits to extract the genomic DNA and RNA (43). Protocols regarding the extraction and processing of DNA and RNA from saliva are described in further detail in the "Examples" section and shown in FIGS. 1 and 4, which demonstrate that one can relatively easily obtain these materials from both blood and saliva.

Blood/Plasma Samples

A number of recent studies have employed DNA or RNA found in blood or serum as a source of information regarding the possible development of cancer (for example, see (74)). Serum has also been used a source from which to determine hypermethylation of specific genes in patients with hormone refractory metastatic prostate cancer (75). Accordingly, in some embodiments blood samples can be obtained from the same patients that provided the tissue samples and stored in the frozen state. After thawing the samples, they can be processed as described in the "Examples" section of the present disclosure. PCR can then be used to look for the presence of HPV DNA, RT PCR or qNPA can be used to look for the presence and level of the selected viral and cellular transcripts, and MS-MLPA can be used to look for the methylation of selected promoter sequences, as described above and in the "Examples" section. In addition to the analyses described more completely for tissues, the presence of anti-HPV antibodies can be detected in serum samples, which could provide evidence of a recent infection.

Saliva

Saliva samples can be obtained, preferably from the same patients that provided the tissue and blood samples, and stored in the frozen state. After thawing, the samples are then processed as described in further detail in the "Examples" section. PCR can be used to look for the presence of HPV DNA, RT PCR or qNPA can be used to look for the presence and level of the selected viral and cellular transcripts, and MS-MLPA can be used to look for the methylation of selected promoter sequences, as described above and in the "Examples" section. Saliva samples can be collected using the collection and preservation kits produced by Oragene. These kits enable the collection and preservation of DNA and RNA from human saliva until processing.

While a limited number of studies have attempted to develop panels of biomarkers for the detection of HNC based on the messages or proteins present in saliva or peripheral blood, none, to our knowledge, has attempted to inform these screening strategies with the current state of our knowledge regarding the biological events that accompany HPV– associated cancer. In contrast, our approach intentionally incorporates what is known about HPV biology and its role in the development of cancer, as well as what has previously been discovered using more global, blinded screens, into our development of a candidate panel. This approach should yield a panel that is less easily swayed by variability between specific assay platforms, as we are screening for biomarkers that are solidly connected to HPV biology.

Matched Sample Sets

In one embodiment, matched sample sets, each of which will include cancer tissue, non-cancerous adjacent tissues, blood/serum and saliva, are obtained from the same individual. For comparison, negative controls (no diagnosed HPV-related, cervical, or HNCs) and positive controls, e.g., from patients with diagnosed HPV+ tonsillar cancer (early stage and late stage), from patients with HPV– head/neck cancer, and from patients with HPV+ cervical cancer, may be obtained. Using this group of matched sets will permit calibration of the panel based on the detection of biomarkers important to head/neck cancer in general, to HPV-associated tonsillar cancer specifically, to HPV-associated cancer in general (both head/neck and cervical), and to HPV-associated cervical cancer.

Analysis of Markers

Each of the samples will be processed as appropriate and each measurement should be made in triplicate. For the RNA measurements, the expression levels of each target message can be compared to expression of the GAPDH gene in the same samples. Changes in expression levels in cancer tissue vs. adjacent normal tissue can be compared to the observed levels in saliva and plasma/serum to see if changes indicative of the presence of cancer can also be detected in saliva and/or plasma/serum. DNA samples isolated from different biological samples from the same donor can be analyzed to see how the methylation measurements from the different materials do or do not correlate.

DNA

DNA can be extracted from tissues using the DNeasy Blood and Tissue Kit (Qiagen). Following DNA extraction, degenerate primers like GP5+/GP6+ (61) can be employed in a PCR protocol to look for the presence of the HPV sequences themselves, as by definition, they are expected to be present in HPV-associated tumors. Once is it confirmed that HPV sequences are present, the HPV type can be determined by cloning and sequencing the PCR product. It has previously been shown that PCR followed by DNA sequencing can be used to detect HPV sequences from oral exfoliated cells (14).

The analysis of several host promoters of interest can be performed using a commercial MS-MLPA (methylation-specific multiplex ligation-dependent probe amplification) kit (MRC Holland) that estimates the methylation status of 25 tumor suppressor genes known to be frequently silenced in cancer. This kit has been used successfully in previous studies of cervical cancer (43). The same MS-MLPA technique can be used for the analysis of other promoters that are not included in the kit; these include both viral and cellular promoters. The LCR and early promoter region of the HPV region can be methylated, and it has been suggested that the DNA methylation state of HPV can vary depending on the viral life cycle and on the presence or absence of integration (62). In addition, global and epigenetic studies of HPV-associated cervical cancers have already identified a set of specific methylation biomarker candidates that may be useful for the analysis of HPV+ head and neck tumors, and the majority of these biomarkers are not included in the available MS-MPLA kit. These 23 biomarkers include such genes as SPARC, TFP12, RRAD, SFRP1 and others. Our experience in utilizing the protocol for MS-MPLA analysis of the CDKN2B and TP73 promoters is described in further detail in the Examples section of the present disclosure. In order to verify that the results obtained from the high-throughput, multiplexed MS-MLPA approach are valid, bisulfite sequencing may be used to confirm the results. A variety of commercially-available kits are available for this purpose (such as the Active Motif MethylDetector Bisulfite Modification Kit).

RNA

RNA extracted from the tissues using Trizol Reagent (Invitrogen) can be quantitatively analyzed for the presence and level of both viral and cellular messages. Viral messages to be analyzed include those for the E2, E5, E6 and E7 genes, as their levels will provide valuable information regarding the current status of the virus and the possible progression of transformation. Specifically, our understanding of the biological events that occur as HPV-associated malignancies develop leads us to predict that in cases where transformation may be occurring, the levels of E6 and E7 expression should be higher than in cases where no transformation is occurring. In the case of E6, one may further analyze for the presence of messages coding for both the large and small isoforms. Finally, the levels of E2 and E5 expression may provide further information regarding viral integration (37).

One may also analyze tissue for the presence and levels of cellular genes whose expression may be changed during the development of HPV-associated HNC. These genes can be selected based on previously-published analyses, including several of the candidates listed in Tables 1 and 2, as well as others drawn from the literature. A preferred set of candidates includes CDKN2B, TP73, CD44, p16, TCAM1, SYCP2, STAG3, CDC2, CEC7, E2Fs, several of the MCMs, cytokeratin 17 and p63. CDKN2B has been shown to be upregulated in HPV-associated cancers (38, 42). CD44, and specifically, certain splice variants of CD44 is of interest, as evidence exists that the presence of specific variants may be associated with the presence of HNC (63-69). p16 (CDKN2A) is another gene which has been associated with tonsillar carcinomas and papillomavirus status (36, 70-72), as well as with HPV-associated cervical cancer (72). TCAM1, SYCP2 and STAG3 are normally testis-specific but were found to be expressed in HPV positive cancer cells (38). Expression of these genes should be negligible in normal cells found in the oral cavity, so detection of them in saliva will be a good indication that transformation is occurring in the head and neck region. In addition to these three genes, the Pyeon group identified a number of additional genes that regulate proliferation; any tumor cells found may display an up-regulation of genes that control the cell cycle by enhancing proliferation. This list includes PCNA (proliferating cell nuclear antigen), CDC2, CDC7, E2Fs, and MCM. Cytokeratin 17 and p63 are also included in the list, as they may be markers for cervical stem cells (73), which have been suggested to serve as target cells for HPV.

Protein

In some embodiments, immunohistochemistry can be employed to look for evidence of expression of viral proteins, such as E6 and E7, in tissues. Some studies have shown an increase in protein expression of certain cellular proteins, such as p16 (36, 70) following HPV infection. Therefore, tissue sections can be examined for up-regulation of these proteins as well.

PCR

In another embodiment, the presence of a HPV DNA, HPV mRNA or host cell mRNA is detected in a biological sample, using polymerase chain reaction (PCR), or real time RT-PCR, techniques. PCR is used to detect the genetic material to identify a current (active) infection, for example early on, before antibodies have been formed. PCR can detect genetic material in various biological samples including, blood, stool, respiratory secretions or body tissue. Amplifying a second genetic region can further increase the specificity of PCR. Primers, which are the key pieces for a PCR test, may be publicly available or can be prepared using known methods. Preferably, both positive and negative controls are used, because negative results don't necessarily indicate that the HPV DNA, mRNA or host cell mRNA is not present or expressed in a subject (false negative). Examples of negative controls, include controls for the extraction procedure and water control for the PCR run. It is also desirable to confirm positive results to avoid "false positives" in which the presence of HPV or host cell biomarkers is indicated in error. Positive controls include a control for extraction and PCR. In addition, the sample can be "spiked" with a weak positive control in order to detect any PCR inhibitory substances that would interfere with the test.

High Throughput Methods

In another embodiment of the invention, high throughput genomic methods are used to detect multiple target nucleic acids that may be present in a biological sample from a subject. These procedures typically use a multiple-well microtiter plate, containing multiple different oligonucleotide probes specific for multiple target agents (nucleic acid: DNA or RNA, or protein) in each well, that may or may not be present in the biological sample, where the probes are attached to the surface of each well. The ability to test several targets simultaneously is known as "multiplexing." The assays are performed using reagents and conditions effective for reaction of the probe with its respective target molecule. High Throughput methods are known in the art, for example, as described in issued U.S. Pat. Nos. 6,232,066, 6,238,869, 6,331,441 and 6,458,533, incorporated by reference in their entirety, herein, and are commercially available (e.g. High Throughput Genomics, Tucson, Ariz.). In the methods of the invention, a high throughput assay can be run using multiple (e.g. 100) plates with "wells" for containing the reactions, such as 96-well microplates, simultaneously. Each well of a plate can have multiple, different tests performed in it, by using an array of corresponding probes. For example, 100 plates, with 96 wells per plate, and each with 16 tests per well, can be used. In this case, each of 9,600 different biological samples can be tested simultaneously, for 16 different parameters or assays. High throughput assays provide much more information for each biological sample, than do assays which test only one target nucleic acid or protein at a time. Thus, it is possible in a single initial high throughput screening assay to determine whether a sample from a subject contains any of several target nucleic acids or proteins.

Nuclease Protection Assay

In one embodiment of the invention, a high throughput method is used, that detects messenger RNA (mRNA) or DNA corresponding to HPV or host cell biomarkers, and does not involve any RNA extraction, amplification, purification or biosynthetic steps. This method is known as the "quantitative nuclease protection assay or "qNPA," (High Throughput Genomics, Inc., Tucson, Ariz.), that can quantitatively measure mRNA, from samples of fewer than 1,000 cells, without extraction or amplification (U.S. Pat. No. 6,238,869, incorporated by reference herein). In essence, the qNPA produces a stoichiometric amount of the specific nuclease protection probe for each gene, or a quantitative amount of a chemical mirror image. All the reagents that bind to the plate are synthetic and structurally unaltered by the assay. Assays can be conducted using a microplate washer, incubator and standard pipetting station. Standard automation and workstations perform all assay steps. Assay results are detected using known imaging devices, such as the Omix Imager™ (HTG, Tucson, Ariz.).

Other methods, including improvements to known methods, and newly developed methods, for rapidly and specifically detecting one or more biomarkers in a biological sample, can be used in the business method of the invention.

EXAMPLES

DNA and RNA Isolation from Saliva and Plasma Samples

Unstimulated saliva samples were collected according the published protocol (58). Samples of 1-3 ml were centrifuged at 2600×g for 5 min at 4° C., then supernatant was collected and used for RNA isolation immediately or snap frozen in liquid nitrogen and kept at −80° C. Plasma samples were obtained from fresh blood samples by centrifugation at 2600×g for 15 min at 4° C., and then processed in the same way as the saliva samples. Nucleic acids from both saliva and blood samples were isolated using the QIAamp Viral RNA kit, using a modified version of the manufacturer's protocol. In this modified protocol, glycogen was used rather than carrier RNA to increase the yield of DNA and RNA. Isolated samples were either used directly for PCR analysis with the indicated DNA probes, or used for purification of RNA. In this case, samples were incubated with DNase using the TURBO DNA-free Kit (Ambion) followed by RNA cleanup with the RNeasy Mini kit. RNA was eluted in 40 µl of water, and 20 µl was used for the first strand cDNA synthesis.

PCR Analysis of DNA Samples.

To determine the presence and estimate the level of DNA in isolated samples, we amplified a sequence that is not normally transcribed in genomic DNA. We used forward (TGT GTT TTC AAA GAC GGT GG, SEQ ID NO:23) and reverse (CAG GCT TTC GCT ATA TGG GC, SEQ ID NO:24) primers that amplify the region upstream of the SFRS6 promoter.

As shown in FIG. 1A, saliva samples consistently contained more DNA than did the plasma samples. This may indicate that the saliva samples contain significantly more cells, which are not separated during centrifugation due to high viscosity. This would be advantageous for our purpose, as it is likely that in cases where HPV-associated HNC is present, exfoliated cells from the affected area will end up in the oral cavity. Saliva may therefore offer a significant advantage over plasma samples as a potential source for biomarkers in HNC.

RT-PCR Analysis of RNA Samples.

Figure 1B:
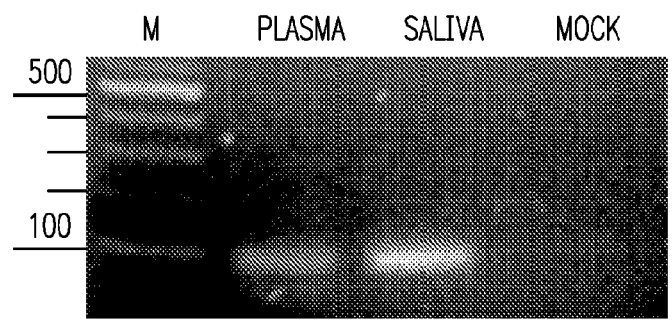
FIG. 1B shows PCR amplification results when the DNA/RNA samples were further purified with RNeasy for RNA cleanup, eluted in 10 µl of water, and 5 µl was used for cDNA synthesis by ImProm-II reverse transcriptase (Promega) in a 20 µl reaction volume. 0.5 µl of the reaction mix was used for amplification of the GAPDH-specific PCR product.

To obtain cDNA from purified samples of plasma and saliva RNA, we used either Superscript III (Invitrogen) or ImProm-II (Promega) Reverse Transcriptase, following the manufacturer's protocols. After cDNA synthesis, PCR was employed to detect the presence of GAPDH mRNA sequences (FIG. 1B). As in case of DNA, saliva samples consistently contained more RNA than did the plasma samples.

This determination was followed by a real-time PCR analysis of the presence and relative levels of a set of additional messages in the samples isolated from saliva and plasma. The list of primers for the 10 genes tested is presented in Table 3.

Ct value and the Ct value of background exceeded 2, and to be marginally present when the Ct value difference was lower than 2 but greater than 0.5. These data show that saliva samples contain DNA and mRNA at considerably higher levels than plasma. Therefore, saliva can be regarded as a useful source in the search for biomarkers, especially with regards to HNC.

MS-MLPA Analysis of the CDKN2B Promoter Region

We chose to test for methylation status using a quantitative version of fragment analysis known as MS-MPLA (methylation-specific multiplex ligation-dependent probe amplification) (59, 60). In this procedure (FIG. 2), the denatured DNA sample is first hybridized with the target-specific probe; this step is then followed by simultaneous ligation and digestion with a methylation sensitive restrictase (such as HhaI). PCR is then employed to amplify the region between the ligated probes. If the sequence is methylated and therefore resistant to digestion with the restriction enzyme, ligation will yield an amplicon that can be amplified by PCR. However, if the sequence was not methylated, the restriction enzyme will have cut the amplicon, and there will be no PCR product (see FIG. 2). An ABI 310 DNA sequencer allows the use of fluorescently-tagged probes in a multiplexed manner for this

TABLE 3

Primers for qPCR

| Gene symbol | Primers | | SEQ ID NO |
|---|---|---|---|
| GAPDH | TGC ACC ACC AAC TGC TTA GC | Sense | SEQ ID NO: 1 |
| | GGC ATG GAC TGT GGT CAT GAG | Antisense | SEQ ID NO: 2 |
| CDKN2A | AGA AAC CTC GGG AAA CTT AGA T | Sense | SEQ ID NO: 3 |
| | CTA CGT TAA AAG GCA GGA CAT T | Antisense | SEQ ID NO: 4 |
| DAPK1 | GCA AAG TAC AAC ACC AGT AAC G | Sense | SEQ ID NO: 5 |
| | CAG GTT GAT TTT GAA CAC AGA G | Antisense | SEQ ID NO: 6 |
| GSTP1 | TCC CTC ATC TAC ACC AAC TAT G | Sense | SEQ ID NO: 7 |
| | AGT CCA GCA GGT TGT AGT CAG | Antisense | SEQ ID NO: 8 |
| KLK10 | ATG AGC ACG ATC TCA TGT TG | Sense | SEQ ID NO: 9 |
| | GAA GAC CTC ACA CTC TTT AGG G | Antisense | SEQ ID NO: 10 |
| SESN3 | ACT ATA CCT GGG AAA ATC ATG G | Sense | SEQ ID NO: 11 |
| | AGT TCT CTC AGG ATA GCA GGT C | Antisense | SEQ ID NO: 12 |
| Fas | GAC ATG GCT TAG AAG TGG AAA | Sense | SEQ ID NO: 13 |
| | TTA GTG TCA TGA CTC CAG CAA | Antisense | SEQ ID NO: 14 |
| CFL1 | CCT TCC CAA ACT GCT TTT GAT | Sense | SEQ ID NO: 15 |
| | CTG GTC CTG CTT CCA TGA GTA | Antisense | SEQ ID NO: 16 |
| NFKB1A | TGA TCC TGA GCT CCG AGA CTT T | Sense | SEQ ID NO: 17 |
| | AGC CCT GGT AGG TAA CTC TGT T | Antisense | SEQ ID NO: 18 |
| CUTL1 | TAA CTC TTA CAG CTT TGC CTT G | Sense | SEQ ID NO: 19 |
| | GGA ATC CAA ACT AGT GTG TTT AGA | Antisense | SEQ ID NO: 20 |

The primers were designed to contain intron-intron junctions or to be located within different introns in order to prevent amplification of genomic DNA sequences. To perform real time PCR, we used the Absolute QRCR SYBR Green kit. For each reaction, we used 1 µl of saliva cDNA ($1/20^{th}$ of total cDNA synthesis reaction mixture) and 2 µl of the plasma samples. Real-time PCR detected the presence of GAPDH, DAPK1, Fas and NFKB transcripts in plasma. On the other hand, saliva from the same donor contained transcripts of all the genes tested except for CFL1, though the SESN3 and GSTP1 gene transcripts were present at marginal levels (FIG. 1C). mRNA was considered to be present in a particular blood or saliva sample if the difference between its analysis. A commercially available kit (MRC-Holland) is designed for the simultaneous analysis of 25 host genes that are frequently methylated in tumors. Due to the quantitative nature of this approach, one will be able to distinguish between situations where both alleles are methylated, one allele is methylated while one is not, and both alleles are un-methylated.

However, this kit does not include HPV-specific probes, and two of the sequences we wish to assess are HPV sequences. For this reason, we developed a modified protocol, using the CDKN2B gene as a model. Modifications were necessary due to our use of a variety of different enzymes that required buffers and temperature conditions that were often incompatible. The CDKN2B gene was selected as our test gene. The first step was to clone the HhaI-containing CDKN2B promoter region of 0.8 Kb into pTOPO. Using primers 5'-TGT GGT TGA GGA ATC CCG TCT CAT-3' (SEQ ID NO:21) and 5'-TGG GAA AGA AGG GAA GAG TGT CGT-3' (SEQ ID NO:22), we amplified the appropriate region from genomic DNA and cloned the fragment into the pTOPO2.1 vector using the TOPO TA cloning kit (Invitrogen). Three independent clones were sequenced, and one of them, which contained no mutations in the amplified region, was selected for further work.

Figure 3:
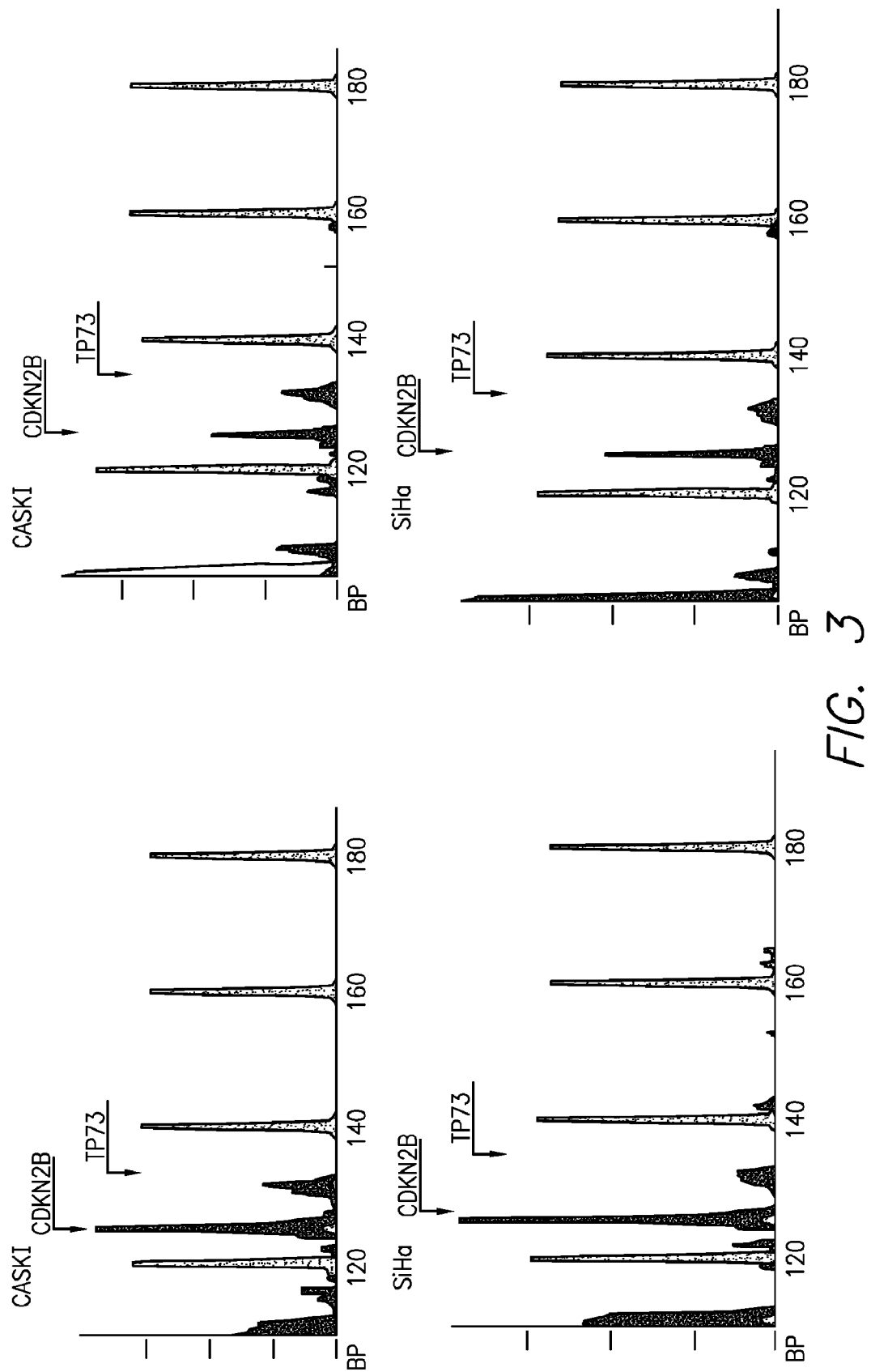
FIG. 3 shows analysis of the methylation status of the CDKN2B and TP73 promoters in two cervical cancer cell lines: CaSki and SiHa. The two panels to the left show undigested samples and the two panels to the right show samples digested with HhaI. The peaks of the MS-MLPA products for each of the two cell lines are shown as arrows.

The plasmid DNA as initially isolated is unmethylated, since *E. coli* does not possess a CpG methylation system. To methylate HhaI sites in the pTOPO-CDKN2B plasmid, we incubated plasmid DNA with HhaI methylase according to the manufacturer's protocol (New England Biolabs), and monitored methylation by resistance to digestion with HhaI restrictase (FIG. 2). As shown in the Figure, the unmethylated plasmid DNA digest consists of a group of short fragments with molecular weights of less than 500 bp, while DNA treated with HhaI methylase prior to digestion remains intact, showing almost complete methylation of the HhaI sites. The modified MS-MLPA protocol was then applied to both the methylated and unmethylated samples. Using this protocol, we were able to distinguish between methylated and unmethylated variants of the CDKN2B plasmid (FIG. 2). To show that this protocol is compatible with other probes, we also used it to monitor methylation of the TP73 promoter region. Using both the CDKN2B and TP73 probe sets, we analyzed methylation of DNA isolated from Siha and Caski cell lines, both of which are derived from HPV16-mediated cervical carcinomas (FIG. 3). These results show that the CDKN2B site is not fully methylated (though it may be hemi-methylated) and that TP73 is methylated in both cell lines, consistent with data obtained previously. (43). These results also demonstrate that our modified protocol can be used for analysis of methylation status. We also tested this protocol for compatibility with a DNA sample isolated from paraffin embedded tissue sections of HPV positive HNC; these results demonstrated that the CDKN2B sequence is hemi-methylated while the TP53 sequence is likely to be unmethylated (data not shown). Together, the results shown in this section of the Examples provide evidence that a reliable MS-MPLA-based protocol can be used to analyze the methylation status of cellular and viral DNA.

Measurement of HPV DNA and Viral RNA

The following example shows the use of qNPA assays for quantitative detection of HPV and/or host cell nucleic acids from HPV-infected cells, cervical clinical samples and saliva. The reagents include a nuclease protection probe that is specific for a specific target, programming linker, detection linker and detection probe. A Universal Array is manufactured by printing 16 different DNA "anchor" sequences, 25 bases each, onto polystyrene microplates. To program this Universal Array, a cocktail of 16 different "programming linker" capture probes (each 50 bases long of synthetic DNA) is added, each in large excess, incubated at 50° C. for 30 min, and then washed. One species of programming linker will hybridize (across 25 bases) to only one anchor, or specific element, of the array. The other 25 base half of the programming linker is designed to hybridize specifically to 25 bases of one specific nuclease protection probe. Thus, the specificity of hybridization of each element is converted to capture a specific set of 16 different nuclease protection probes.

The sample processing and assay protocol includes the following steps. A lysis reagent is added to the sample, e.g., cells, tissue, blood or saliva, incubated at 95° C. for 10 min then cooled and frozen or tested immediately. If not already in the lysis solution, a cocktail of nuclease protection probes is added (each 50 bases long, synthetic DNA, each designed to hybridize to a different target gene), and incubation is carried out for 6 hr at 60° C. S1 nuclease is then added and incubated for 60 min at 50° C., during which time all the nonspecific RNA and DNA is destroyed, all the excess single stranded nuclease protection probes and non-hybridized target RNA are destroyed and only the specific probe/target hybrid duplexes remain, thereby providing the quantitative stoichiometry of the assay. Base is added to dissociate the probes from the target RNA and destroy the released target RNA. The solution is transferred onto a previously programmed Array Plate (described above), and the probes captured during an overnight incubation at 50° C. Detection linker can be added at the time the sample is transferred, or added separately and incubated for 60 min The media is removed and HRP-labeled detection probe is added and incubated at 37° C. for 30 min, then washed to remove unbound probe. Luminescence substrate is added and the entire microplate is imaged to measure the level of each gene. The amount of luminescence indicates how much of each target gene was present in the sample; the position in the array identifies which gene is being measured.

Table 4 depicts the sensitivity and specificity of measurement of HPV 16 viral DNA and RNA (E6/E7) as well as host mRNA from 100 or 10 Cash cells infected with HPV 16 in a background of 10,000 HeLa cells infected with HPV 18. The % CVs are indicated, without normalization. There are 600 copies of viral DNA integrated in to the genome of each Caski cell. The Digene HPV hc2 hybrid capture assay has a limit of detection of 20 Caski cells. Thus, qNPA is more sensitive than the current FDA approved diagnostic.

TABLE 4

HPV GENE MEASUREMENT

| | HPV18 HeLa Cells | | 10 HPV16 Caski Cells | |
|---|---|---|---|---|
| | Avg Signal | % CV | Avg Signal | % CV |
| Host GADPH | 4624 | 13% | 5808 | 12% |
| Host B2Mg | 158 | 22% | 215 | 20% |
| Host PPIA | 1739 | 16% | 2769 | 10% |
| Host Actin | 2973 | 17% | 6741 | 11% |
| Avg CV | | 17% | | 13% |
| Viral DNA | 0 | NA | 115 | 16% |
| Viral RNA | 0 | NA | 66 | 22% |

Table 5 presents the qNPA data from cervical PAP smears collected in Preservcyte during routine office visits. All samples were tested by the Digene hc2 assay and determined to be positive, weakly positive or negative, then tested blind by a qNPA assay. Because the host cell mRNA was measured in the same array, the qNPA assay was able to identify a "bad" sample—one which simply did not contain sufficient material to determine infectivity but had been reported out from the hc2 assay as negative. The qNPA assay also picked up two presumptive negative (by hc2 assay) samples that were actually positive, a result confirmed by an independent lab using PCR. The rest of the samples demonstrated the ability of the qNPA assay to accurately identify every weakly positive sample and additional negative samples. Thus, the ability to use qNPA to measure host cell mRNA simultaneously with HPV viral DNA and mRNA, and to differentiate strains of HPV, has been validated.

TABLE 5

SPECIFICITY OF HPV MEASUREMENT FROM CLINICAL CERVICAL SAMPLES

| | Bad Sample | | Presumptive Negative | | Weak Positive | | Weak Positive | | Weak Positive | | True Negative | | True Negative | |
|---|---|---|---|---|---|---|---|---|---|---|---|---|---|---|
| | Avg Signal | CV | Avg Signal | CV | Avg Signal | CV | Avg Signal | CV | Avg Signal | CV | Avg Signal | CV | AvG Signal | CV |
| GAPDH | 66 | 9% | 1111 | 13% | 4120 | 27% | 4461 | 24% | 6458 | 5% | 567 | 8% | 5696 | 18% |
| B2Mg | 38 | 20% | 113 | 24% | 150 | 19% | 147 | 25% | 209 | 16% | 197 | 15% | 170 | 33% |
| Viral DNA | | | 2155 | 15% | 80 | 15% | 98 | 29% | 129 | 18% | | | | |
| Viral RNA | | | 853 | 20% | 23 | 18% | 30 | 26% | 42 | 24% | | | | |
| PPIA | 136 | 10% | 520 | 20% | 1616 | 18% | 1905 | 24% | 2681 | 10% | 1526 | 9% | 2163 | 25% |
| Actin | 137 | 9% | 2040 | 21% | 2703 | 21% | 2975 | 22% | 4328 | 11% | 753 | 11% | 3489 | 19% |
| Avg CV | | 12% | | 19% | | 20% | | 25% | | 14% | | 11% | | 24% |

Figure 4:
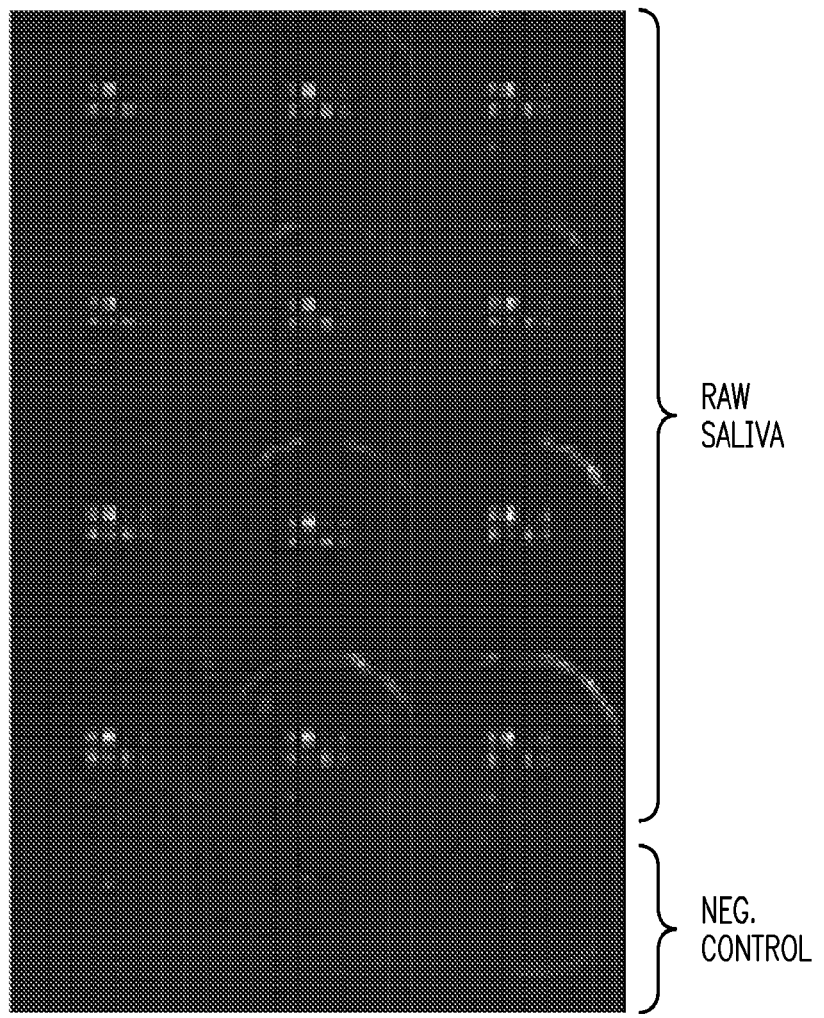
FIG. 4 shows analysis of gene expression when normal control saliva was mixed 1:1 with lysis reagent, then processed for qNPA. The data for replicates is shown for saliva versus negative control (no saliva). The level of genes with measured expression are detailed in Table 6. Note the repeatability of measurement.

We tested the basic concept of whether we could measure relevant biomarker genes from saliva using gNPA™ by measuring several relevant host cell genes from normal spit. Normal control saliva was mixed 1:1 with lysis reagent, then processed for qNPA. FIG. 4 (images from ArrayPlate) and Table 6 demonstrate the measurement of these genes from normal spit. The images for replicates are shown in FIG. 4 for saliva versus negative control (no saliva). The level of genes with measured expression is detailed in Table 6. Note the repeatability of measurement.

TABLE 6

SALIVA GENE EXPRESSION

| Gene | Average | Std Dev | CV | |
|---|---|---|---|---|
| GAPDH | 1000 | 0 | 0% | |
| IL-8 | 1247 | 124 | 10% | |
| IL1-B | 5672 | 637 | 11% | |
| DUSP1 | 513 | 94 | 18% | |
| OAZ1 | 789 | 516 | 65% | |
| SAT | 1682 | 275 | 16% | |
| S100P | 556 | 52 | 9% | |
| ANXA2 | 349 | 521 | 15% | |
| Avg % CV | | | 13% | without OAZ1 |
| Avg % CV | | | 21% | with OAZ1 |

REFERENCES

The following references are incorporated by reference in their entirety:
1. Hunter K D, Parkinson E K, Harrison P R. Profiling early head and neck cancer. Nat Rev Cancer 2005; 5(2):127-35.
2. Bastian P J, Palapattu G S, Yegnasubramanian S, et al. CpG island hypermethylation profile in the serum of men with clinically localized and hormone refractory metastatic prostate cancer. J Urol 2008; 179(2):529-34; discussion 34-5.
3. Burd E M. Human papillomavirus and cervical cancer. Clin Microbiol Rev 2003; 16(1):1-17.
4. Boulet G A, Horvath C A, Berghmans S, Bogers J. Human papillomavirus in cervical cancer screening: important role as biomarker. Cancer Epidemiol Biomarkers Prev 2008; 17(4):810-7.
5. Ragin C C, Modugno F, Gollin S M. The epidemiology and risk factors of head and neck cancer: a focus on human papillomavirus. J Dent Res 2007; 86(2):104-14.
6. Venuti A, Badaracco G, Rizzo C, Mafera B, Rahimi S, Vigili M. Presence of HPV in head and neck tumours: high prevalence in tonsillar localization. J Exp Clin Cancer Res 2004; 23(4):561-6.
7. Campisi G, Panzarella V, Giuliani M, et al. Human papillomavirus: its identity and controversial role in oral oncogenesis, premalignant and malignant lesions (review). Int J Oncol 2007; 30(4):813-23.
8. Gillison M L, Koch W M, Capone R B, et al. Evidence for a causal association between human papillomavirus and a subset of head and neck cancers. J Natl Cancer Inst 2000; 92(9):709-20.
9. Ha P K, Califano J A. The role of human papillomavirus in oral carcinogenesis. Crit Rev Oral Biol Med 2004; 15(4): 188-96.
10. Mork J, Lie A K, Glattre E, et al. Human papillomavirus infection as a risk factor for squamous-cell carcinoma of the head and neck. N Engl J Med 2001; 344(15):1125-31.
11. D'Souza G, Kreimer A R, Viscidi R, et al. Case-control study of human papillomavirus and oropharyngeal cancer. N Engl J Med 2007; 356(19):1944-56.
12. Gillison M L. Human papillomavirus-associated head and neck cancer is a distinct epidemiologic, clinical, and molecular entity. Semin Oncol 2004; 31(6):744-54.
13. Gillison M L, Lowy D R. A causal role for human papillomavirus in head and neck cancer. Lancet 2004; 363(9420):1488-9.
14. Smith E M, Ritchie J M, Summersgill K F, et al. Human papillomavirus in oral exfoliated cells and risk of head and neck cancer. J Natl Cancer Inst 2004; 96(6):449-55.
15. Herrero R, Castellsague X, Pawlita M, et al. Human papillomavirus and oral cancer: the International Agency for Research on Cancer multicenter study. J Natl Cancer Inst 2003; 95(23):1772-83.
16. Chaturvedi A K, Engels E A, Anderson W F, Gillison M L. Incidence trends for human papillomavirus-related and -unrelated oral squamous cell carcinomas in the United States. J Clin Oncol 2008; 26(4):612-9.
17. Syrjanen S. Human papillomavirus (HPV) in head and neck cancer. J Clin Virol 2005; 32 Suppl 1:S59-66.
18. Doorbar J. The papillomavirus life cycle. J Clin Virol 2005; 32 Suppl 1:S7-15.
19. Grm H S, Massimi P, Gammoh N, Banks L. Crosstalk between the human papillomavirus E2 transcriptional activator and the E6 oncoprotein. Oncogene 2005; 24(33): 5149-64.
20. Bouvard V, Storey A, Pim D, Banks L. Characterization of the human papillomavirus E2 protein: evidence of trans-activation and trans-repression in cervical keratinocytes. Embo J 1994; 13(22):5451-9.
21. Demeret C, Desaintes C, Yaniv M, Thierry F. Different mechanisms contribute to the E2-mediated transcriptional repression of human papillomavirus type 18 viral oncogenes. J Virol 1997; 71(12):9343-9.

22. Steger G, Corbach S. Dose-dependent regulation of the early promoter of human papillomavirus type 18 by the viral E2 protein. J Virol 1997; 71(1):50-8.
23. Steger G, Ham J, Yaniv M. E2 proteins: modulators of papillomavirus transcription and replication. Methods Enzymol 1996; 274:173-85.
24. Huibregtse J M, Scheffner M, Howley P M. Localization of the E6-AP regions that direct human papillomavirus E6 binding, association with p53, and ubiquitination of associated proteins. Mol Cell Biol 1993; 13(8):4918-27.
25. Liu Y, Baleja J D. Structure and function of the papillomavirus E6 protein and its interacting proteins. Front Biosci 2008; 13:121-34.
26. Tungteakkhun S S, Duerksen-Hughes P J. Cellular binding partners of the human papillomavirus E6 protein. Arch Virol 2008; 153:397-408.
27. Dyson N, Howley P M, Munger K, Harlow E. The human papilloma virus-16 E7 oncoprotein is able to bind to the retinoblastoma gene product. Science 1989; 243(4893): 934-7.
28. Munger K, Werness B A, Dyson N, Phelps W C, Harlow E, Howley P M. Complex formation of human papillomavirus E7 proteins with the retinoblastoma tumor suppressor gene product. Embo J 1989; 8(13):4099-105.
29. Wise-Draper T M, Wells S I. Papillomavirus E6 and E7 proteins and their cellular targets. Front Biosci 2008; 13:1003-17.
30. Alani R M, Hasskarl J, Grace M, Hernandez M C, Israel M A, Munger K. Immortalization of primary human keratinocytes by the helix-loop-helix protein, Id-1. Proc Natl Acad Sci USA 1999; 96(17):9637-41.
31. Hebner C M, Laimins L A. Human papillomaviruses: basic mechanisms of pathogenesis and oncogenicity. Rev Med Virol 2006; 16(2):83-97.
32. Laimins L A. The biology of human papillomaviruses: from warts to cancer. Infect Agents Dis 1993; 2(2):74-86.
33. Lowy D R, Kirnbauer R, Schiller J T. Genital human papillomavirus infection. Proc Natl Acad Sci USA 1994; 91(7):2436-40.
34. Komori H, Ichikawa S, Hirabayashi Y, Ito M. Regulation of UDP-glucose:ceramide glucosyltransferase-1 by ceramide. FEBS Letters 2000; 475:247-50.
35. Hafner N, Driesch C, Gajda M, et al. Integration of the HPV16 genome does not invariably result in high levels of viral oncogene transcripts. Oncogene 2008; 27(11):1610-7.
36. Kim S H, Koo B S, Kang S, et al. HPV integration begins in the tonsillar crypt and leads to the alteration of p16, EGFR and c-myc during tumor formation. Int J Cancer 2007; 120(7): 1418-25.
37. Torrente M C, Ampuero S, Abud M, Ojeda J M. Molecular detection and typing of human papillomavirus in laryngeal carcinoma specimens. Acta Otolaryngol 2005; 125(8):888-93.
38. Pyeon D, Newton Mass., Lambert P F, et al. Fundamental differences in cell cycle deregulation in human papillomavirus-positive and human papillomavirus-negative head/neck and cervical cancers. Cancer Res 2007; 67(10):4605-19.
39. Chung C H, Parker J S, Karaca G, et al. Molecular classification of head and neck squamous cell carcinomas using patterns of gene expression. Cancer Cell 2004; 5(5): 489-500.
40. Cromer A, Carles A, Millon R, et al. Identification of genes associated with tumorigenesis and metastatic potential of hypopharyngeal cancer by microarray analysis. Oncogene 2004; 23(14):2484-98.
41. Ginos M A, Page G P, Michalowicz B S, et al. Identification of a gene expression signature associated with recurrent disease in squamous cell carcinoma of the head and neck. Cancer Res 2004; 64(1):55-63.
42. Slebos R J, Yi Y, Ely K, et al. Gene expression differences associated with human papillomavirus status in head and neck squamous cell carcinoma. Clin Cancer Res 2006; 12(3 Pt 1):701-9.
43. Henken F E, Wilting S M, Overmeer R M, et al. Sequential gene promoter methylation during HPV-induced cervical carcinogenesis. Br J Cancer 2007; 97(10):1457-64.
44. Worsham M J, Chen K M, Meduri V, et al. Epigenetic events of disease progression in head and neck squamous cell carcinoma. Arch Otolaryngol Head Neck Surg 2006; 132(6):668-77.
45. Wu X, Bayle J H, Olson D, Levine A J. The p53-mdm-2 autoregulatory feedback loop. Genes Dev 1993; 7:1126-32.
46. Chen K, Sawhney R, Khan M, et al. Methylation of multiple genes as diagnostic and therapeutic markers in primary head and neck squamous cell carcinoma. Arch Otolaryngol Head Neck Surg 2007; 133(11):1131-8.
47. Wang S S, Smiraglia D J, Wu Y Z, et al. Identification of novel methylation markers in cervical cancer using restriction landmark genomic scanning Cancer Res 2008; 68(7): 2489-97.
48. Lai H C, Lin Y W, Huang T H, et al. Identification of novel DNA methylation markers in cervical cancer. Int J Cancer 2008; 123(1):161-7.
49. Li Y, Elashoff D, Oh M, et al. Serum circulating human mRNA profiling and its utility for oral cancer detection. J Clin Oncol 2006; 24(11):1754-60.
50. Mathur S P, Mathur R S, Creasman W T, Underwood P B, Kohler M. Early non-invasive diagnosis of cervical cancer: beyond Pap smears and human papilloma virus (HPV) testing. Cancer Biomark 2005; 1(2-3):183-91.
51. Badoual C, Bouchaud G, Agueznay Nel H, et al. The soluble alpha chain of interleukin-15 receptor: a proinflammatory molecule associated with tumor progression in head and neck cancer. Cancer Res 2008; 68(10):3907-14.
52. Pai N P, Barick R, Tulsky J P, et al Impact of round-the-clock, rapid oral fluid HIV testing of women in labor in rural India. PLoS Med 2008; 5(5):e92.
53. Amado L A, Villar L M, de Paula V S, Gaspar A M. Comparison between serum and saliva for the detection of hepatitis A virus RNA. J Virol Methods 2008; 148(1-2): 74-80.
54. Streckfus C, Bigler L, Dellinger T, et al. Reliability assessment of soluble c-erbB-2 concentrations in the saliva of healthy women and men. Oral Surg Oral Med Oral Pathol Oral Radiol Endod 2001; 91(2):174-9.
55. Herr A E, Hatch A V, Throckmorton D J, et al. Microfluidic immunoassays as rapid saliva-based clinical diagnostics. Proc Natl Acad Sci USA 2007; 104(13):5268-73.
56. Denny P, Hagen F K, Hardt M, et al. The proteomes of human parotid and submandibular/sublingual gland salivas collected as the ductal secretions. J Proteome Res 2008; 7(5): 1994-2006.
57. Zimmermann B G, Park N J, Wong D T. Genomic targets in saliva. Ann N Y Acad Sci 2007; 1098:184-91.
58. Navazesh M. Methods for collecting saliva. Ann N Y Acad Sci 1993; 694:72-7.
59. Langerak P, Nygren A O, Schouten J P, Jacobs H. Rapid and quantitative detection of homologous and non-homologous recombination events using three oligonucleotide MLPA. Nucleic Acids Res 2005; 33(22):188.

60. Nygren A O, Ameziane N, Duarte H M, et al. Methylation-specific MLPA (MS-MLPA): simultaneous detection of CpG methylation and copy number changes of up to 40 sequences. Nucleic Acids Res 2005; 33(14):128.
61. Snijders P J, van den Brule A J, Schrijnemakers H F, Snow G, Meijer C J, Walboomers J M. The use of general primers in the polymerase chain reaction permits the detection of a broad spectrum of human papillomavirus genotypes. J Gen Virol 1990; 71 (Pt 1):173-81.
62. Kalantari M, Lee D, Calleja-Macias I E, Lambert P F, Bernard H U. Effects of cellular differentiation, chromosomal integration and 5-aza-2'-deoxycytidine treatment on human papillomavirus-16 DNA methylation in cultured cell lines. Virology 2008; 374(2):292-303.
63. Resch A, Xing Y, Modrek B, Gorlick M, Riley R, Lee C. Assessing the impact of alternative splicing on domain interactions in the human proteome. J Proteome Res 2004; 3(1):76-83.
64. Franzmann E J, Reategui E P, Carraway K L, Hamilton K L, Weed D T, Goodwin W J. Salivary soluble CD44: a potential molecular marker for head and neck cancer. Cancer Epidemiol Biomarkers Prev 2005; 14(3):735-9.
65. Franzmann E J, Reategui E P, Pedroso F, et al. Soluble CD44 is a potential marker for the early detection of head and neck cancer. Cancer Epidemiol Biomarkers Prev 2007; 16(7): 1348-55.
66. Bloor B K, Rajarajan A, Jaafary-Haghighat K, Odell E W. Transcription and expression of CD44 variant exons by oro-pharyngeal squamous cell carcinomas. Int J Oncol 2002; 21(4):907-13.
67. Bloor B K, Jelvagharan M, White K N, Odell E W. Characterization of CD44 splicing patterns in normal keratinocytes, dysplastic and squamous carcinoma cell lines. Int J Oncol 2001; 18(5): 1053-9.
68. Nelson A D, Grandis J R. The role of CD44 in HNSCC. Cancer Biol Ther 2007; 6(1):125-6.
69. Yaqin M, Runhua L, Fuxi Z. Analyses of Bcl-2, Survivin, and CD44v6 expressions and human papillomavirus infection in cervical carcinomas. Scand J Infect Dis 2007; 39(5): 441-8.
70. Begum S, Cao D, Gillison M, Zahurak M, Westra W H. Tissue distribution of human papillomavirus 16 DNA integration in patients with tonsillar carcinoma. Clin Cancer Res 2005; 11(16):5694-9.
71. Wittekindt C, Gultekin E, Weissenborn S J, Dienes H P, Pfister H J, Klussmann J P. Expression of p16 protein is associated with human papillomavirus status in tonsillar carcinomas and has implications on survival. Adv Otorhinolaryngol 2005; 62:72-80.
72. Smith E M, Wang D, Kim Y, et al. P16INK4a expression, human papillomavirus, and survival in head and neck cancer. Oral Oncol 2008; 44(2):133-42.
73. Martens J E, Arends J, Van der Linden P J, De Boer B A, Helmerhorst T J. Cytokeratin 17 and p63 are markers of the HPV target cell, the cervical stem cell. Anticancer Res 2004; 24(2B):771-5.
74. Bastian P J, Palapattu G S, Yegnasubramanian S, et al. Prognostic value of preoperative serum cell-free circulating DNA in men with prostate cancer undergoing radical prostatectomy. Clin Cancer Res 2007; 13(18 Pt 1):5361-7.

What is claimed is:

1. A method of detecting biomarkers associated with head and neck tumors in a patient comprising:
    (a) providing a first patient sample from the patient, wherein the first patient sample is selected from the group consisting of saliva, whole blood, white blood cells, serum, plasma and biopsy tissue from the throat, oropharynx or mouth of the patient;
    (b) contacting the first patient sample with:
        (1) a first reagent that specifically binds to one or more than one HPV (human papillomavirus) biomarker, and allowing the first reagent to bind to the one or more than one HPV biomarker if the HPV biomarker is present in the first patient sample;
    where the first reagent is an oligonucleotide;
    where the one or more than one HPV biomarker is mRNA; and
        (2) a second reagent that specifically binds to one or more than one host cell biomarker, wherein the host cell biomarker is differentially expressed in head and neck tumor cells as compared to normal cells, and allowing the second reagent to bind to the one or more than one host cell biomarker;
    where the host cell biomarker is MCM8;
    where the first reagent binds to the one or more than one HPV biomarker if the HPV (human papillomavirus) biomarker is present in the first patient sample, and the second reagent binds to the one or more than one host cell biomarker simultaneously;
    (c) simultaneously detecting the presence or absence of the HPV biomarker in the first patient sample and determining the expression level of the host cell biomarker in the first patient sample; and
    (d) comparing the expression level of the host cell biomarker in the first patient sample to an expression level of the host cell biomarker from at least one reference sample, wherein the reference sample is a comparable biological sample obtained from a disease-free subject.

2. The method of claim 1, wherein the HPV mRNA is selected from the group consisting of E2 mRNA, E6 mRNA and E7 mRNA.

3. The method of claim 1, wherein the one or more than one HPV biomarker is a plurality of HPV biomarkers.

4. The method of claim 1, wherein the one or more than one host cell biomarker is a plurality of host cell biomarkers.

5. The method of claim 1, further comprising comparing the expression level of the host cell marker in the first patient sample to the expression level of the host cell marker for one or more than one additional reference sample, wherein the additional reference sample is a comparable biological sample obtained from a patient with an HPV positive head and neck tumor or a patient with an HPV negative head and neck tumor.

6. The method of claim 1, further comprising:
    (e) contacting a second patient sample from the patient with:
        (1) a reagent that specifically binds to a HPV biomarker, and
        (2) a reagent that specifically binds to a host cell marker differentially expressed in head and neck tumor cells as compared to normal cells;
    (f) detecting the presence or absence of the HPV marker; and
    (g) determining the expression level of the host cell biomarker in the second patient sample;
    wherein the first patient sample is saliva and the second patient sample is selected from the group consisting of whole blood, blood cells, serum, plasma, or a tissue sample from the throat, oropharynx or mouth.

7. A method of detecting biomarkers associated with head and neck tumors in a patient comprising:
    (a) providing a patient sample from the patient, wherein the patient sample is selected from the group consisting of saliva, whole blood, white blood cells, serum, plasma and biopsy tissue from the throat, oropharynx or mouth of the patient;
    (b) contacting the patient sample with:
        (1) a first reagent that specifically binds to one or more than one HPV (human papillomavirus) biomarker, and allowing the first reagent to bind to the one or more than one HPV biomarker if the HPV biomarker is present in the patient sample; and
    where the first reagent is an oligonucleotide;
    where the one or more than one HPV biomarker is mRNA;
        (2) a second reagent that specifically binds to one or more than one host cell biomarker, wherein the host cell biomarker is differentially expressed in HPV positive head and neck tumor cells as compared to HPV negative head and neck tumor cells, and allowing the second reagent to bind to the one or more than one host cell biomarker;
    where the host cell biomarker is MCM8;
    where the first reagent binds to the one or more than one HPV biomarker if the HPV biomarker is present in the patient sample, and the second reagent binds to the one or more than one host cell biomarker simultaneously;
    (c) simultaneously detecting the presence or absence of the HPV biomarker in the patient sample and determining the expression level of the host cell biomarker in the patient sample; and (d) comparing the expression level of the host cell biomarker in the patient sample to an expression level of the host cell biomarker from at least one reference sample, wherein the reference sample is a comparable biological sample obtained from a patient with an HPV negative head and neck tumor.

\* \* \* \* \*

UNITED STATES PATENT AND TRADEMARK OFFICE
CERTIFICATE OF CORRECTION

| | | |
|---|---|---|
| PATENT NO. | : 8,715,926 B2 | Page 1 of 1 |
| APPLICATION NO. | : 13/130934 | |
| DATED | : May 6, 2014 | |
| INVENTOR(S) | : Penelope J. Duerksen-Hughes, Maria Filippova and Valeri Filippov | |

It is certified that error appears in the above-identified patent and that said Letters Patent is hereby corrected as shown below:

In the Specification

Column 7, lines 24-25: delete "FIG. 1 shows PCR amplification with DNA-specific and RNA-specific primers."

Column 7, lines 44-45: delete "FIG. 2 shows analysis of the differentially methylated pTOPO plasmid containing the CDK2B promoter region."

Column 22, line 43: replace "may also provided" with --may also be provided.--

Figure 1C:
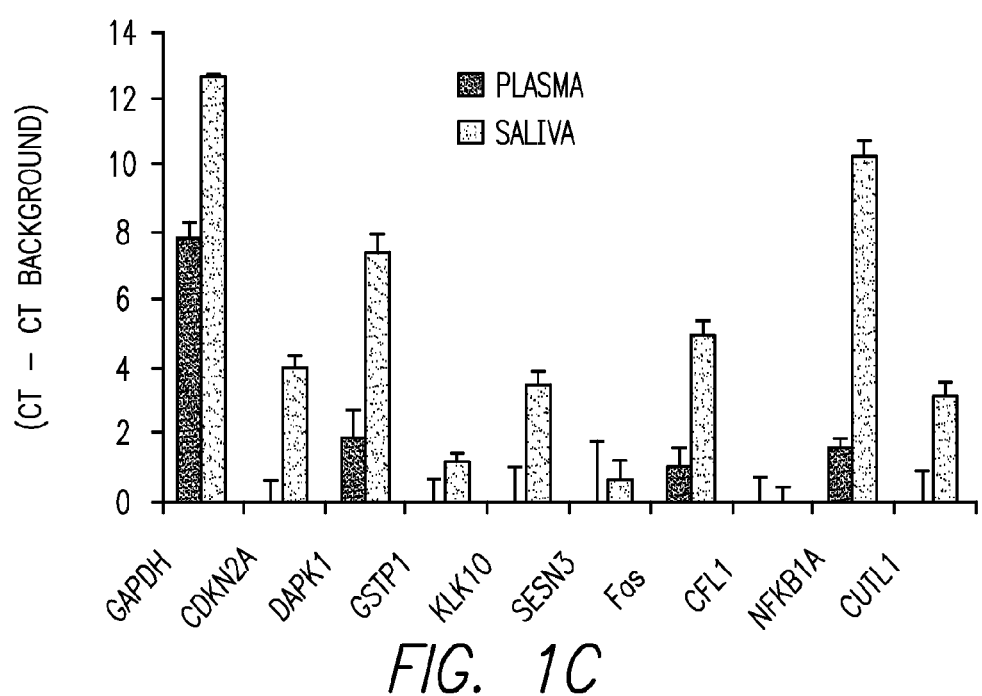
FIG. 1C. shows expression levels of selected genes in plasma and saliva RNA samples. Real-time PCR was performed using the Absolute QPCR SYBR Green kit (ABgene) using 1 µl of standard cDNA synthesis reaction for saliva samples and 2 µl for plasma samples. Ct values for blank PCR probes were subtracted from the Ct values obtained for plasma and saliva probes. In some cases the subtracted values were negative and were considered to be equal to zero.
Figure 2A:
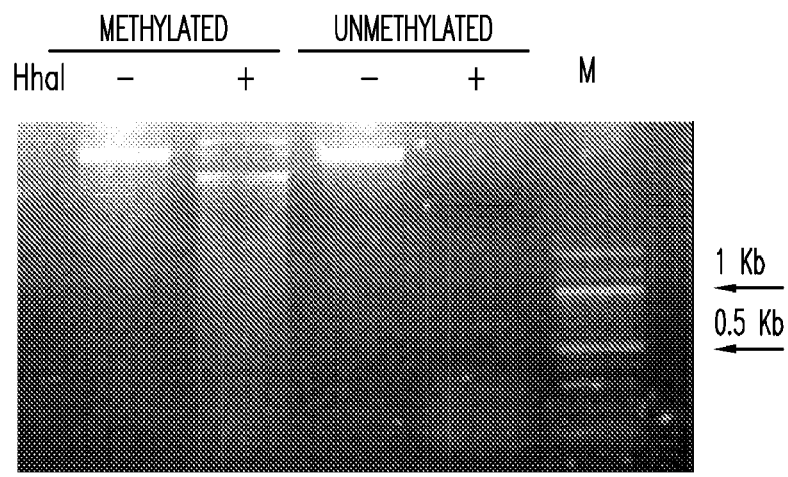
FIG. 2A shows the results following preparation and analysis of the methylated form of pTOPO-CDKN2. Unmethylated pTOPO-CDKN2 was methylated with HhaI methylase, then incubated with HhaI. The methylated, but not the unmethylated version, displays resistance to HhaI-mediated digestion.
Figure 2B:
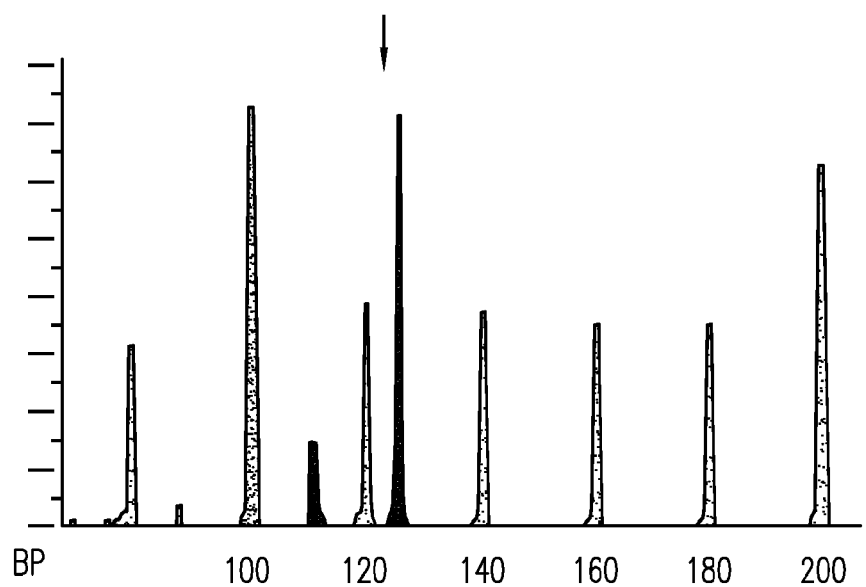
FIGS. 2B, 2C, 2D and 2E are graphs that display the MS-MPLA analyses of methylated and unmethylated forms of the plasmid. Black arrows point to the peaks corresponding to the generated PCR products, which are indicative of an intact DNA sequence at the restriction site.
Figure 2C:
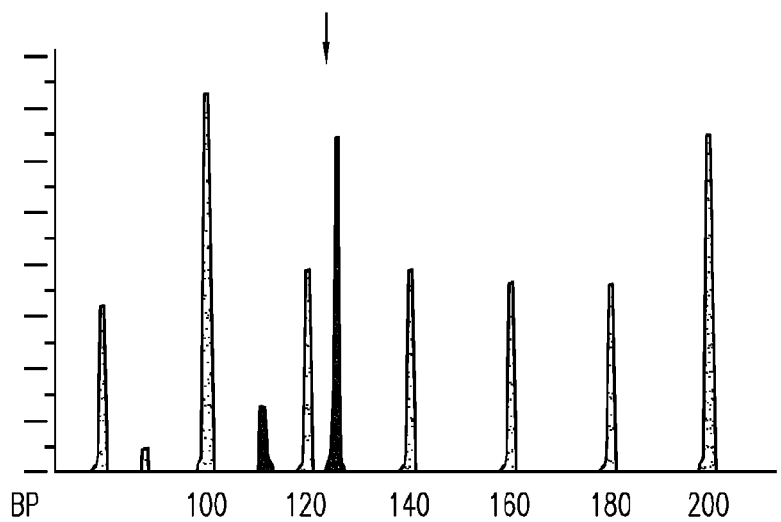
Figure 2D:
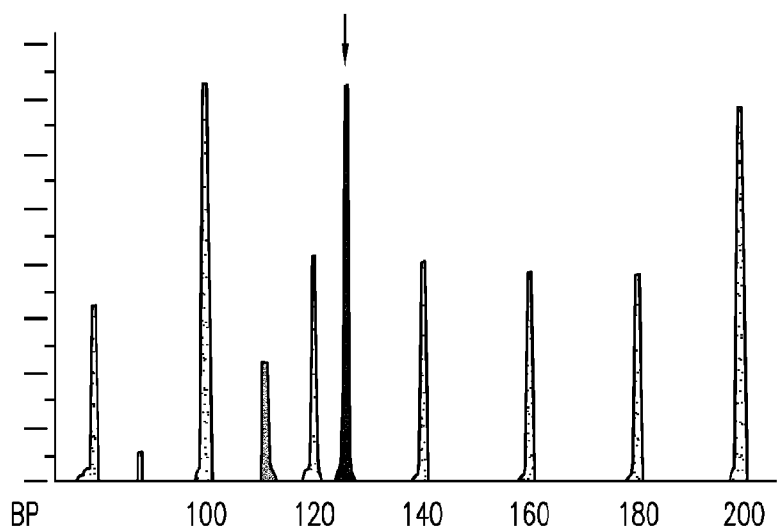
Figure 2E:
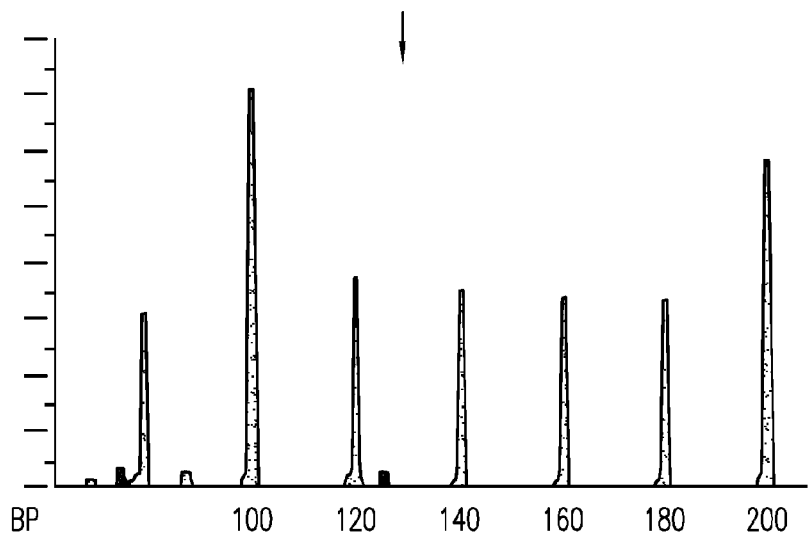

Column 22, lines 53-54: replace "FIGS. 1 and 4" with --FIGS. 1A, 1B, 1C and 4--

Column 28, line 12: delete "In this procedure (FIG. 2)" and replace with --Referring now to FIGS. 2A, 2B, 2C, 2D and 2E, in this procedure--

Column 28, line 22: delete "(see FIG. 2)"

Column 29, line 12: delete "The plasmid DNA" and replace with --Referring again to FIGS. 2A, 2B, 2C, 2D and 2E, the plasmid DNA--

Column 29, line 18: delete "(FIG. 2)"

Column 29, line 26: delete "(FIG. 2)"

Signed and Sealed this
Eighth Day of July, 2014

Michelle K. Lee
*Deputy Director of the United States Patent and Trademark Office*